United States Patent [19]

Meguro et al.

[11] Patent Number: 5,254,565
[45] Date of Patent: Oct. 19, 1993

[54] QUINOLINE DERIVATIVES, THEIR PRODUCTION AND USE

[75] Inventors: Kanji Meguro, Nishinomiya; Hitoshi Ikeda, Higashiosaka, both of Japan

[73] Assignee: Takeda Chemical Industries, Ltd., Osaka, Japan

[21] Appl. No.: 807,813

[22] Filed: Dec. 16, 1991

Related U.S. Application Data

[63] Continuation of Ser. No. 377,136, Jul. 10, 1989, abandoned.

[30] Foreign Application Priority Data

Jul. 12, 1988 [JP]  Japan ................... 63-174137
Aug. 29, 1988 [JP]  Japan ................... 63-214266
Jul. 27, 1989 [JP]  Japan ................... 1-75925

[51] Int. Cl.⁵ ................ C07D 215/60; C07D 215/38; A61K 31/47
[52] U.S. Cl. ................... 514/312; 514/313; 546/153; 546/159; 546/162
[58] Field of Search .............. 546/153, 159, 162, 160; 514/312, 313

[56] References Cited

U.S. PATENT DOCUMENTS 3,798,226  3/1974  Meguro et al. .............. 546/159
3,819,634  6/1974  Megoro et al. .............. 546/159
3,862,152  1/1975  Kuwada et al. ............. 546/162

OTHER PUBLICATIONS

Grant and Hackh's Chemical Dictionary (1987, McGraw-Hill, New York), p. 14.

*Primary Examiner*—Mukund J. Shah
*Assistant Examiner*—E. C. Ward
*Attorney, Agent, or Firm*—Wegner, Cantor, Mueller & Player

[57] ABSTRACT

Quinoline derivatives of the formula:

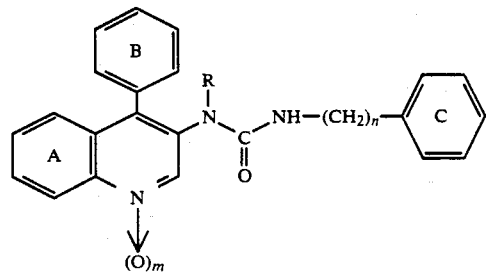

(I)

, wherein R is hydrogen, alkyl or aralkyl; m and n are 0 or 1, and each of rings A, B and C can have substituents, which are useful as inhibitors for acyl-CoA:Cholesterolacyltransferase.

9 Claims, No Drawings

QUINOLINE DERIVATIVES, THEIR PRODUCTION AND USE

This application is a continuation of U.S. application Ser. No. 07/377,136 filed Jul. 10, 1989 now abandoned.

BACKGROUND OF THE INVENTION

1. Field of the Invention

This invention relates to quinoline derivatives which possess excellent inhibitory action for acyl-CoA:cholesterol acyltransferase (ACAT). The compounds of this invention inhibit the absorption of cholesterol through the intestinal tract of a mammal and also restrain the accumulation of cholesterol ester at the arterial wall, and accordingly are useful as a drug for preventing and treating hypercholesterolemia, atherosclerosis and various diseases caused thereby (e.g. ischemic cardiac diseases such as myocardial infarction, cerebrovascular disturbance such as cerebral infarction, cerebral apoplexy, etc.).

2. Description of the Prior Art

In the specification of U.S. Pat. No. 3,862,152, there mention specifically 6-chloro-4-phenyl-3-phenylureido)quinoline (Compound A), 6-chloro-3-[3-(4-chlorophenyl)ureido]-4-phenylquinoline (Compound B) and 3-(3-benzylureido)-6, 7-dimethoxy-4-phenylquinoline (Compound C), which possess antiulcer action.

Also, 6-chloro-3-phenyl(or p-chlorophenyl) acetamido- 4-phenylquinoline is known to be effective as antitrichomonas or antiulcer agent (see U.S. Pat. No. 3,798,226).

There has not been any report and description that the above mentioned compounds possess pharmacological activity useful as a drug for arteriosclerosis such as ACAT inhibiting activity and blood cholesterol lowering activity, and these points have not been studied so far.

Therefore, it has not been known that the compounds A, B and C and their analogue compounds are useful as a drug for arteriosclerosis.

The inventors of this invention studied the physiological activities of the above mentioned compounds A, B and C and their analogue compounds, and found that known compounds such as compound B etc. and new compounds which are not described concretely in the above mentioned publications possess strong ACAT inhibitory activity and are useful as a drug for arteriosclerosis.

SUMMARY OF THE INVENTION

This invention relates to (1) an ACAT inhibiting composition containing a quinoline derivative of the general formula:

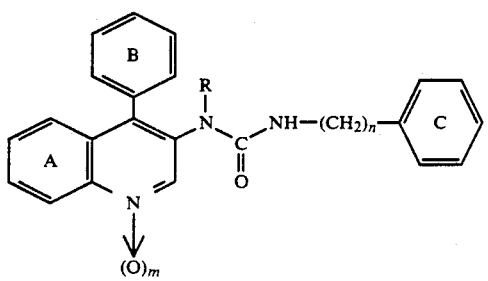

(I)

, wherein R is a hydrogen atom, or an alkyl or aralkyl group, m and n are 0 or 1, and each ring of A, B and C can have substituent(s) or its salt;

(2) a new quinoline derivative of the formula (I), wherein m is 1; or m is 0 and the ring B has substituent(s); or m is 0, the ring B has no substituent and the ring C is substituted with fluorine atom(s), in other words in case of m=1, each of rings A, B and C can have substituent(s), and in case of m=0, each of rings A and C can have substituent(s) and ring B has substituent(s), or ring C is substituted with fluorine atom(s) when ring B has no substituent, or its salt; and (3) a method for the preparation of the new quinoline derivative and its salt mentioned in the above (2).

DESCRIPTION OF THE PREFERRED EMBODIMENT

Preferably, the alkyl groups for R in the formula (I) are straight or branched-chain ones having 1-8 carbon atoms, such as methyl, ethyl, propyl, isopropyl, butyl, isobutyl, sec-butyl, tert-butyl, pentyl, isopentyl neopentyl, hexyl, heptyl, octyl, and the like.

Preferably, the aralkyl groups for R are phenylalkyl groups having 7-9 carbon atoms, such as benzyl, 1-phenylethyl, 2-phenylethyl, 2-phenylpropyl, 3-phenylpropyl, and the like, in which the benzene ring can have similar substituent(s) to those of the ring A, B or C as mentioned later. And further R can be heteroarylalkyl groups having 5-8 carbon atoms which possess a hetero ring such as thiophene, furan or pyridine instead of the benzene ring of the above mentioned phenylalkyl group. Preferable example of R is a hydrogen atom.

The symbol n is 0 or 1, and preferably n is 0.

Each ring of A, B and C can have substituent(s). Examples of the substituents are a halogen atom, an optionally halogenated lower alkyl group, an optionally halogenated lower alkoxy group, an optionally halogenated lower alkylthio group, nitro group, an optionally esterified carboxy group, hydroxy group a $C_{1-4}$ acyloxy (e.g. formyloxy, acetoxy, propionyloxy, butyryloxy, etc.) and a $C_{1-3}$ acyl group (e.g. formyl, acetyl, propionyl, etc.). The halogen atom in these groups can be fluorine, chlorine, bromine or iodine atom.

The optionally halogenated lower alkyl group can be straight or branched-chain lower alkyl groups of 1-6 carbon atoms and these lower alkyl groups may be substituted with two to five halogen atoms, such as methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, 2-trifluoromethylethyl, butyl, 4,4,4-trifluorobutyl, isobutyl, sec-butyl, tert-butyl, pentyl, isopentyl, neopentyl, 5,5,5-trifluoropentyl, 4-trifluoromethylbutyl, hexyl, 6,6,6-trifluorohexyl or 5-trifluoromethylpentyl.

The optionally halogenated lower alkoxy group and the optionally halogenated lower alkylthio group can be those formed by the combination of the above mentioned lower alkyl group or halogenated lower alkyl group and an oxygen atom or a sulfur atom.

The optionally esterified carboxy groups can be carboxy groups esterified by an alkyl of 1-6 carbon atoms such as methyl, ethyl, propyl, isopropyl, butyl, isobutyl, sec-butyl, tert-butyl, pentyl or hexyl.

The substituent(s) on the ring A, B and C can be at any position of each ring, and these substituents may be the same or different, and the number of the substituent(s) may be 1 to 4. The suitable position(s) of the substituent(s) are 6- and/or 8- positions of the quinoline nucleus for the ring A, 2- position for the ring B, and 2- and/or 4- positions for the ring C. The suitable substituent(s) on the ring C can be chlorine or fluorine atom(s), and 2,4-difluoro-substituted ring C is especially preferable.

The salts of the quinoline derivative (I) can be the salts with an inorganic or organic acid such as hydrochloric acid, hydrobromic acid, sulfuric acid, phosphoric acid, methanesulfonic acid, fumaric acid, maleic acid, citric acid or tartaric acid, or the salt with an alkaline metal or alkali earth metal, such as sodium, potassium or calcium.

Representative examples of the quinoline derivatives of the general formula (I) are the following compounds.

(i) Quinoline derivatives of the general formula ($I^a$):

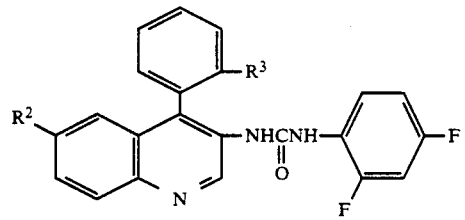

(I$^a$)

, wherein $R^2$ and $R^3$ are, the same or different, a halogen atom or a $C_{1-4}$ alkyl group, and their salts.

The halogen atoms for $R^2$ and $R^3$ can be chlorine, bromine or fluorine. The $C_{1-4}$ alkyl groups for $R^2$ and $R^3$ can be methyl, ethyl, n-propyl, i-propyl, n-butyl, etc. Preferable examples for $R^2$ are chlorine, methyl, ethyl and i-propyl and preferable examples for $R^3$ are chlorine and methyl.

(ii) Quinoline derivatives of the general formula ($I^b$):

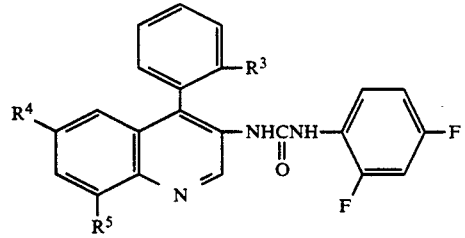

(I$^b$)

, wherein $R^4$ and $R^5$ are, the same or different, a $C_{1-4}$ alkyl group and $R^3$ has the same meaning as defined above, and their salts.

The $C_{1-4}$ alkyl groups for $R^4$ and $R^5$ can be the same as mentioned for $R^3$ in the above. Preferably, both of $R^4$ and $R^5$ are methyl.

The quinoline derivative of the general formula (I) and its salt can be prepared, for example, by reacting a compound of the general formul (II$^a$):

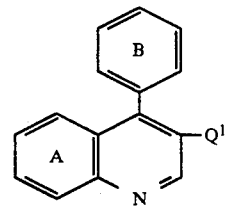

(II$^a$)

or its salt with a compound of the general formula (III$^b$):

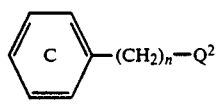

(III$^b$)

or its salt,
, wherein $Q^2$ is —NCO when $Q^1$ is

$$\begin{array}{c} R \\ | \\ -NH \end{array}$$

or $Q^2$ is —NH when $Q^1$ is —NCO or

$$\begin{array}{c} R^1 \\ | \\ -NCOX, \end{array}$$

$R^1$ is an alkyl or aralkyl group, X is a halogen atom, and the other symbols have the same meanings as defined above.

The alkyl and aralkyl groups for $R^1$ can be those as mentioned for R in the above. The halogen atom for X can be Cl or Br.

The following shows more specific methods for the preparation of the compounds (I)

[Method A]

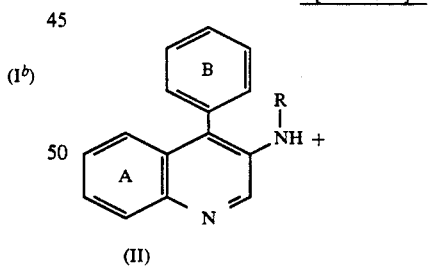

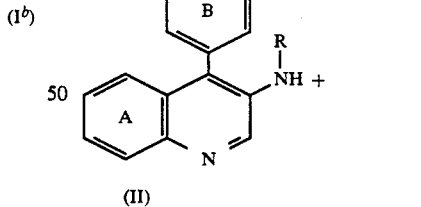

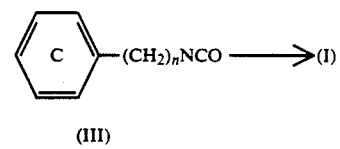

[The symbols in the formulas have the same meanings as above]

[Method B]
(in case of R = H)

-continued
[Method B]

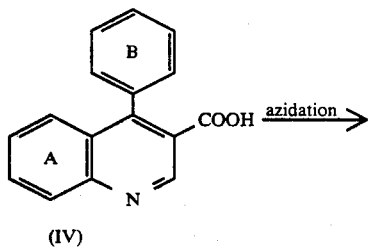
(IV)

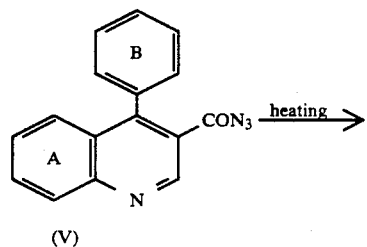
(V)

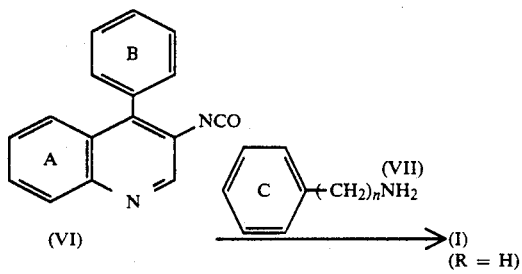
(VI)

[The symbols in the formulas have the same meanings as above]

[Method C]
(in case of R ≠ H)

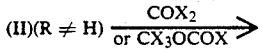

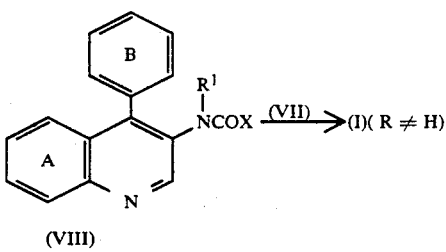
(VIII)

[The symbols in the formulas have the same meanings as above]

[Method D]

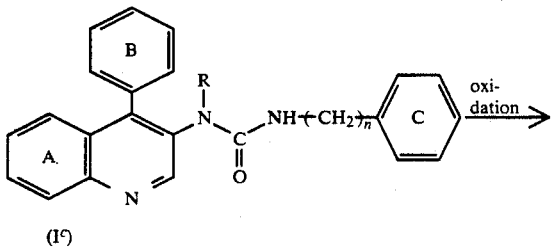
(I^c)

-continued
[Method D]

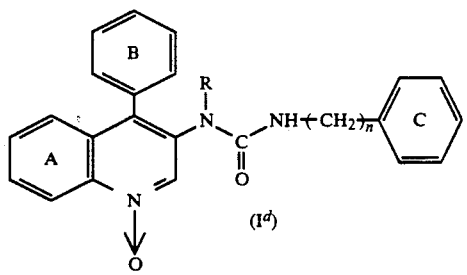
(I^d)

[The symbols in the formulas have the same meanings as above]

The above mentioned compounds (II^a), (III^b) and (II)–(VIII) can be used in the form of a salt thereof as mentioned before for the compound (I).

Method A

The compound (I) and salt thereof can be prepared by reacting a 3-aminoquinoline derivative(II) or its salt with an isocyanate ester (III).

This reaction is usually carried out in an appropriate solvent. The solvent to be used can be any inert solvent, for example, ethers such as ethyl ether, diisopropyl ether, dimethoxyethane, tetrahydrofuran and dioxane; aromatic hydrocarbons such as benzene, toluene and xylene; esters such as methyl acetate and ethyl acetate; ketones such as acetone and methyl ethyl ketone; pyridine; N,N-dimethylformamide and the like. The reaction is usually carried out at about 0° C.–150° C., preferably at about 15° C.–120° C. The amount of the compound (III) to be used is usually about 1–5 equivalent, and preferably about 1–3 equivalent to the compound (II). The reaction time is usually 5–70 hours and preferably 10–30 hours, though it varies with the kinds of the starting materials and solvents to be used, reaction temperature, etc.

Method B

The compound (I) where R is hydrogen atom can be prepared by azidating a quinoline-3-carboxylic acid (IV) to afford a compound (V), heating it to afford a 3-isocyanatoquinoline (VI) and finally reacting thus obtained compound (VI) with an amine (VII).

Any known methods for converting a carboxylic acid to an acid azide can be applied in the first step of this process. For example, the compound (IV) can be converted to a compound (V) by using diphenylphosphoryl azide (DPPA) as an azidating agent. This reaction can be usually carried out in an inert solvent as used in the above Method A. The reaction may be conducted in the presence of a base such as triethylamine, tributylamine or N-methylmorpholine. The reaction is usually carried out at about 0° C.–50° C., preferably at about 10° C.–40° C. The amount of DPPA to be used is usually about 1–2 equivalent, preferably about 1–1.5 equivalent to the compound (IV). Thus produced compound (V) is usually converted to the isocyanatoquinoline (VI) by heating without isolation, though the compound (V) can be isolated and purified by a conventional method. This conversion reaction is preferably carried out in a solvent used for the azidation. The conversion reaction is carried out under heating usually at about 60° C.–150° C., preferably at about 80° C.–120° C.

Thus produced compound (VI) is isolated by a known method or reacted in the form of a reaction mixture, without isolation, with a compound (VII) to give an object compound (I) where R is a hydrogen atom. The reaction with a compound (VII) can be carried out in a similar solvent to those used in the Method A. The reaction is usually carried out at about 20° C.-130° C., preferably at about 60° C.-120° C. The amount of the compound (VII) to be used is usually about 1-3 equivalent, preferably about 1-2 equivalent to the compound (VI). The reaction time is not restricted as far as the object of the reaction is achieved.

Method C

The object compound (I) where R is not a hydrogen atom can be prepared by Method C, too.

This method is conducted at first by reacting a starting compound (II) where R is not a hydrogen atom with a compound of the formula: $COX_2$ or $CX_3OCOX$ (wherein the symbols have the same meanings as above), for example, phosgene, or trichloromethyl chlorocarbonate (phosgene dimer) to give a compound (VIII). This reaction can be carried out in an inert solvent similar to those used in the Method A. The reaction can be carried out in the presence of a base such as triethylamine, tributylamine, N-methylmorpholine, pyridine or quinoline, if necessary. The reaction can be usually carried out at about 0° C.-60° C., preferably at about 10° C. to 40° C. In a case where phosgene, trichloromethyl chlorocarbonate or the like is used, the amount of these reagents is usually about 1-6 equivalent, preferably about 2-5 equivalents of phosgene to the compound (II) where R is not a hydrogen atom.

Thus produced compound (VIII) is isolated by a known means or reacted in the form of a reaction mixture, without isolation, with a compound (VII) to give a compound (I) where R is not a hydrogene atom. This reaction can also be carried out in an inert solvent similar to those used in the above Method A. The reaction can be accelerated in the presence of a base as mentioned in the above process for preparing the compound (VIII), if necessary. The reaction can be usually carried out at about 20° C.-150° C., preferably at about 60° C.-120° C. And further, 4-dimethylaminopyridine can be added to the reaction mixture for accelerating the reaction.

Method D

The object compound (I) where m=1, namely, the compound ($I^d$) can be prepared by oxidizing an object compound (I) where m=0, namely, the compound ($I^c$). This reaction can be carried out by using hydrogen peroxide or an organic peracid such as performic acid, peracetic acid, pertrifluoroacetic acid, perbenzoic acid or m-chloroperbenzoic acid. Though the reaction condition depends on the kind of the oxidizing agent to be used, the reaction can be carried out in a solvent such as formic acid, acetic acid, trifluoroacetic acid, and aqueous solvent thereof, chloroform, dichloromethane, etc., usually at about 10° C.-100° C., preferably at about 20° C.-80° C. The amount of the oxidizing agent to be used is about 1-10 mols, preferably about 1-5 mols for 1 mol of the compound (IC).

Among the compounds (I) obtained in the above Metohds A-D, a compound having lower alkoxy group(s) in the ring A, B or C can be converted into a compound having hydroxy group(s), if necessary, by reacting with boron tribromide or the like. This reaction is usually carried out in a solvent (e.g. dichloromethane, chloroform, carbon tetrachloride, benzene, toluene, etc.), at about −20° C.-80° C., preferably at about 0° C.-30° C. The amount of the boron tribromide to be used is about 1-10 equivalents, preferably about 1-5 equivalents to a lower alkoxy group.

When the compounds (I) prepared by the above methods contain an esterified carboxy or acyloxy group in any of the rings A, B and C, these groups if required can be converted into a carboxy or hydroxy group, respectively, upon hydrolysis. The hydrolysis reaction can be usually conducted with an alkali metal or alkali earth metal hydroxide such as sodium hydroxide, potassium hydroxide or barium hydoxide in the presence of a solvent (e.g., an alcohol such as methanol, ethanol or propanol, or the like.) The reaction temperature is at about 0° C.-100° C., preferably about 20° C.-80° C.

The object compounds (I) obtained in the above methods can be isolated and purified by a known method for isolation and purification (e.g. condensation, extraction by a solvent, column chromatography, recrystallization, etc.)

When a compound (I) having basic nitrogen atom(s) is obtained in the free form, or (and) when acidic group(s) such as a carboxy group exist in the molecule in the free form, their salts can be formed by a conventional method. Further, when a compound (I) is obtained as a salt, it can be converted to its free form by a conventional method.

The compounds (I) possess excellent inhibiting action for acyl-CoA : cholesterol-acyltransferase (ACAT), and its acute toxicity and toxicity by repeated administration are low.

It is known that ACAT is an enzyme relating to the estrerification of cholesterol with high fatty acids in cells, and plays an important role in the absorption of cholesterol through the small intestine and accumulation of cholesterol ester in the cells. Accordingly, ACAT inhibitors can inhibit the absorption of dietary cholesterol through the intestinal tract, restrain the rise of blood cholesterol level restrain the accumulation of cholesterol ester in the cells at the arteriosclerotic lesion and also prevent the progress of atherosclerosis.

The compounds (I) of the present invention are useful as a safe drug for preventing and treating hypercholesterolemia, atherosclerosis and diseases caused thereby (e.g. ischemic cardiac diseases such as myocardial infarction, cerebrovascular disturbances such as cerebral infarction, cerebral apoplexy, etc.) in mammals (e.g., mouse, rat, hamster, rabbit, cat, dog, horse, cattle, sheep, monkey, human, etc.).

When a compound represented by the general formula (I) is used as a medicine for the above diseases, it can be administered orally or parenterally in a form of powder, granule, tablet, capsule, injection, etc. which can be prepared by mixing with an optional pharmaceutically acceptable carrier, excipient or diluent. The compound (I) is preferably administered orally when it is used for, the purpose of inhibiting the absorption of cholesterol. Dosage of the compound (I) depends on the kind of the compound, administration route, condition and age of the patient, etc. For example, when a compound (I) is administered orally to an adult patient having hypercholesterolemia, about 0.005-50 mg, preferably about 0.05-10 mg, more preferably about 0.2-4 mg of the compound is administered per 1 kg of weight of the patient for one day, preferably divided into 1-3 times a day.

The starting compounds for preparing the compounds (I) of this invention can be prepared as follows.

[Method E]

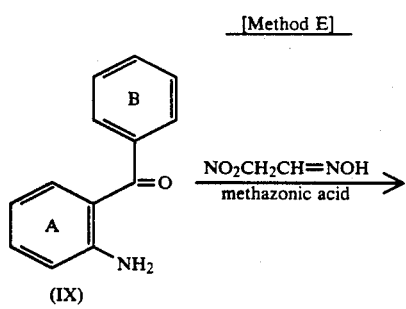
(IX)

NO₂CH₂CH=NOH / methazonic acid →

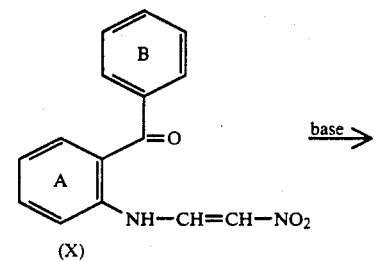
(X)

base →

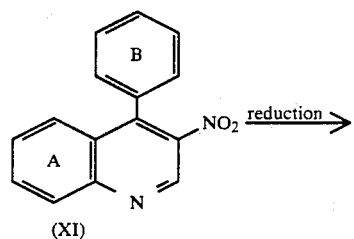
(XI)

reduction →

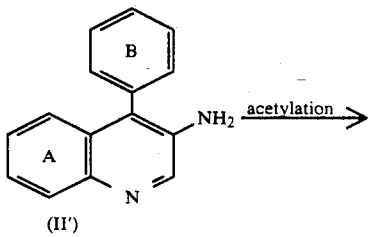
(II')

acetylation →

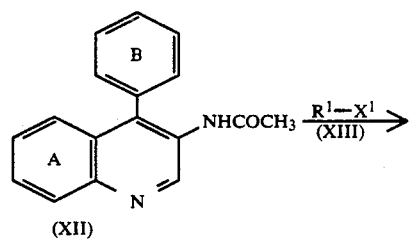
(XII)

R¹—X¹ / (XIII) →

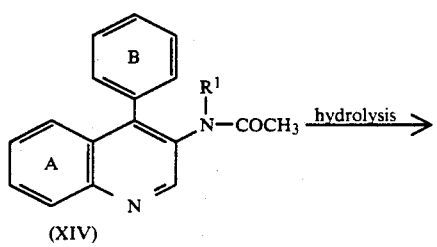
(XIV)

hydrolysis →

-continued
[Method E]

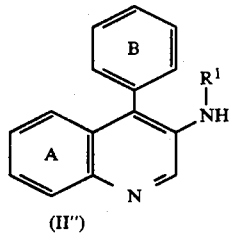
(II'')

, wherein $X^1$ is a leaving group, and the other symbols have the same meanings as defined above.

[Method F]

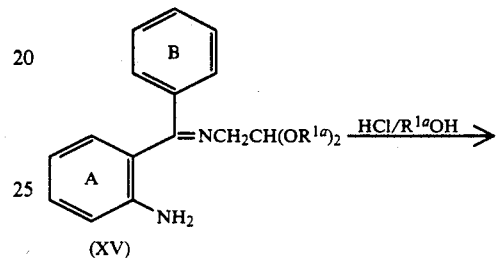
(XV)

HCl/R¹ᵃOH →

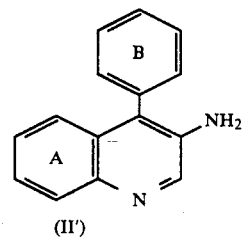
(II')

, wherein $R^{1a}$ is a lower alkyl group, and the other symbols have the same meanings as defined above.

[Method G]

(IX) $\xrightarrow{R^{1a}OCH=C(COOR^{1a})_2 \atop (XVI)}$

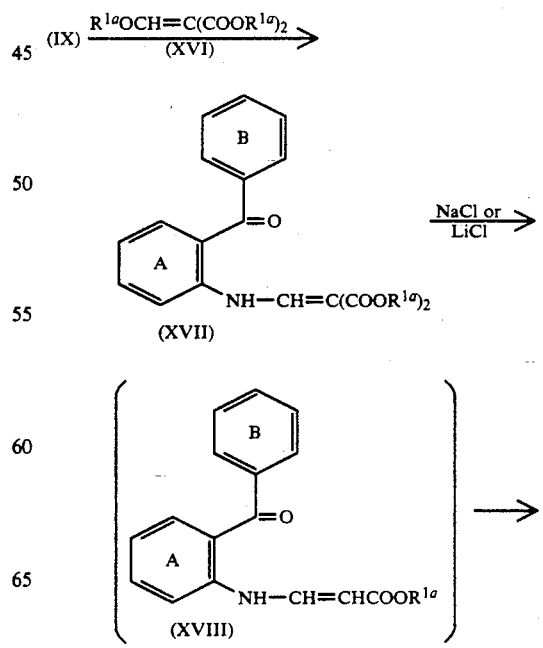

NaCl or LiCl →

[Method G]

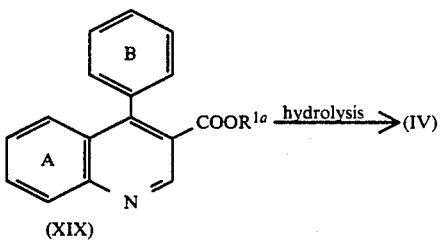

, wherein each symbol has the same meaning as defined above.

Method E

Methods for preparing 3-aminoquinoline (II') from 2-aminobenzophenone (IX) as the starting material through the compounds (X) and (XI) are described in Journal of Chemical Society, page 3914 (1953) and Japanese Patent Publication No. 6474/1973. The compound (II') can be prepared by these methods or a method similar thereto. Acetylation of a compound (II') can be conducted by a method described in U.S. Pat. No. 3,798,226 or Yakugaku Zasshi, vol. 93, page 1263 (1973) or by a method similar thereto to give a compound (XII).

The compound (XII) is then reacted with a compound (XIII) to give a compound (XIV), and thus obtained compound (XIV) is hydrolyzed to give a compound (II'').

The reaction of a compound (XII) with a compound (XIII) can be carried out in a solvent (e.g. tetrahydrofuran, dimethoxyethane, N,N-dimethylformamide, etc.). The reaction can be accelerated in the presence of a base (e.g. sodium hydride, potassium hydride, sodium methylate, sodium ethylate, sodium amide, potassium t-butoxide, etc.). The reaction is usually carried out at about $-10°$ C.$-120°$ C., preferably at about $0°$ C.$-100°$ C. The leaving group for $X^1$ in this reaction can be a halogen (e.g. chlorine, bromine, iodine, etc.), a $C_{1-4}$ alkanesulfonyloxy group (e.g. methanesulfonyloxy group, ethanesulfonyloxy group, etc.), a $C_{1-4}$ alkoxysulfonyloxy group (e.g. methoxysulfonylaxy group, ethoxysulfonyloxy group, etc.), a $C_{6-10}$ arylsulfonyloxy group (e.g. benzenesulfonyloxy group, p-toluenesolfonyloxy group, etc.) and the like. The amounts of the base and the compound (XIII) are usually 1-3 equivalents to the compound (XII), respectively. Thus obtained compound (XIV) is hydrolyzed to give a compound (II'). The hydrolysis reaction can be usually carried out in a solvent (e.g. alcohol such as methanol, ethanol, propanol, acetic acid, etc.). The reaction is suitably conducted by using a mineral acid (e.g. hydrochloric acid, hydrobromic acid, sulfuric acid, etc.) usually in an amount of about 2-20 mols, preferably about 3-15 mols for 1 mol of the compound (XIV). The reaction can be carried out at about $60°$ C.$-120°$ C., preferably at about $70°$ C.$-100°$ C.

Further, the compounds (II'') can be prepared by reacting a compound (I') with a compound (XIII). This reaction can be carried out in a solvent (e.g. carbon tetrachloride, chloroform, methylene chloride, acetone, tetrahydrofuran, dimethoxyethane, N,N-dimethylformamide, etc.) in the presence of a base such as potassium carbonate, sodium carbonate, triethylamine, etc., if necessary. The reaction temperature is usually about $-20°$ C.$-100°$ C., preferably abou $0°$ C.$-60°$ C. The amount of the compound (XIII) to be used is about 1-5 mols, preferably about 1-2 mols for 1 mol of the compound (II').

Method F

This method can be carried out by the process described in U.S. Pat. No. 3,798,226 or Yakugaku Zasshi, Vol. 93, page 1263 (1973) or by a method similar thereto.

Method G

The reaction of a 2-aminobenzophenone compound (IX) with an alkoxymethylenemalonic acid diester (XVI) can be carried out by the method described in Canadian Journal of Chemistry, Vol. 47, page 489 (1969) or by a method similar thereto. The obtained compound (XVII) is then reacted with sodium chloride or lithium chloride under heating to give a quinoline-3-carboxylic acid ester (XIX). This reaction is preferably carried out in a solvent such as dimethylsulfoxide, sulfolane, N,N-dimethylformamide, etc. The reaction is conducted by heating the reaction mixture at about $120°$ C.$-220°$ C., preferably at about $150°$ C.$-200°$ C. The amount of the sodium chloride or lithium chloride to be used is usually about preferably about 2-10 equivalents to the compound (XVII). It is supposed that a compound (XVIII) is formed as an intermediate in this reaction, and (XVIII) is cyclized by dehydration to give a compound (XIX). Thus obtained compound (XIX) is hydrolyzed by an alkali to give a compound (IV). This hydrolysis reaction is usually carried out in a solvent (e.g. methanol, ethanol, propanol, etc.). The reaction can be accelerated in the presence of an alkaline metal or alkali earth metal hydroxide such as sodium hydroxide, potassium hydroxide or barium hydroxide. The reaction can be carried out at about $20°$ C.$-100°$ C., preferably at about $30°$ C.$-90°$ C.

The compounds (II'), (II'') and (IV) obtained in the above Methods, E, F and G can be used as the starting material of the present invention after isolation by a conventional manner or in the form of a reaction mixture without isolation.

Further, 3-nitro compounds (XI) having a substituted-thio group in the ring A or B can be prepared, for example, by the following reaction scheme.

[Method H]

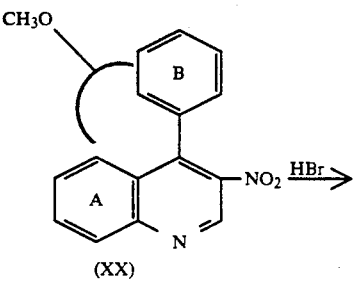

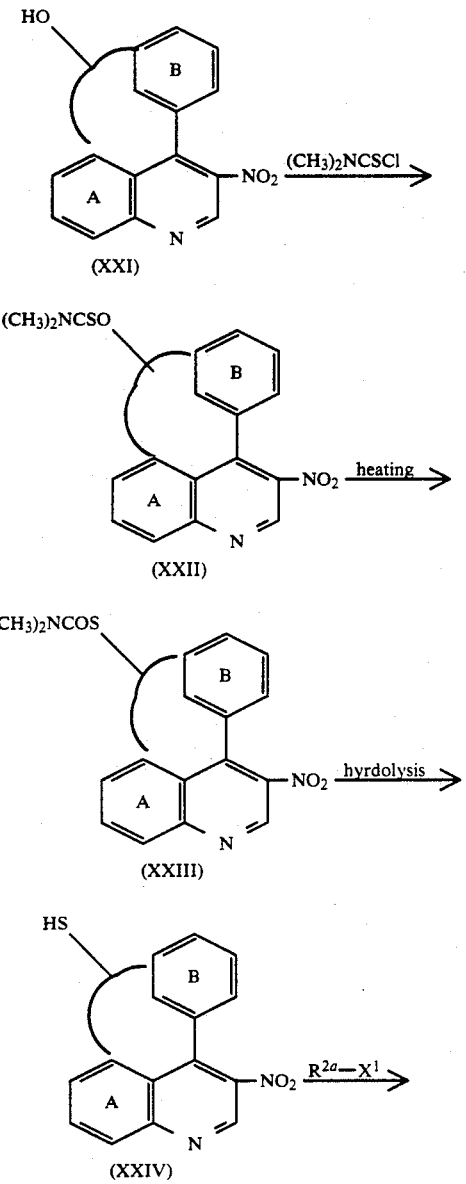

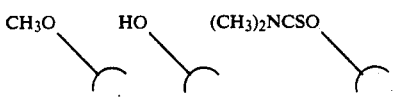

wherein mean the presence of a substituent, $CH_3O-$, $HO-$, $(CH_3)_2NCSO-$, $HS-$ or $R^{2a}-S-$ in the ring A or (and) B, respectively, $R^{2a}$ is an optionally halogenated lower alkyl group, and X' has the same meaning as defined above.

Method H

First, a compound (XXI) is prepared by demethylation of a compound (XX) having methoxy group(s) in the ring A or (and) B by using hydrobromic acid. This reaction is usually carried out by heating under reflux and by using an aqueous solution of hydrobromic acid as a slovent. Acetic acid can be added to the reaction mixture for dissolving the compound, if necessary.

The obtained phenol compound (XXI) is then reacted with N,N-dimethylthiocarbamoyl chloride to give a compound (XXII). This reaction is preferably carried out in an inert solvent (e.g. diethyl ether, dioxane, tetrahydrofuran, chloroform, dichloromethane, ethyl acetate, N,N-dimethylformamide). The reaction can be usually carried out at about $-10°$ C.-$80°$ C., preferably at about $0°$ C.-$60°$ C. The amount of N,N-dimethylthiocarbamoyl chloride to be used is usually about 1-2 equivalents, preferably about 1-1.5 equivalents to the compound (XXI).

The compound (XXII) can be converted to a compound (XXIII) by heating at about $150°$ C.-$250°$ C., preferably at about $170°$ C.-$230°$ C. This conversion reaction is usually carried out by heating a compound (XXII) at a temperature higher than its melting point without using any solvent.

The hydrolysis reaction of a compound (XXIII) can be usually carried out under an alkaline condition. The reaction proceeds favorably in a solvent (e.g. methanol, ethanol, propanol, 2-methoxyethanol, dioxane, dimethoxyethane, etc.) in the presence of sodium hydroxide, potassium hydroxide, barium hydroxide, etc. The reaction temperature is usually about $10°$ C.-$100°$ C., preferably about $20°$ C.-$90°$ C.

The alkylation reaction of a compound (XXIV) is carried out by reacting with a compound of the formula $R^{2a}-X^1$ in a solvent (e.g. methanol, ethanol, propanol, dimethoxyethane, dioxane, tetrahydrofuran, acetone, N,N-dimethylformamide, etc.) in the presece of a base (e.g. potassium carbonate, sodium carbonate, potassium hydroxide, sodium hydroxide, etc.). The reaction temperature is usually $-10°$ C.-$100°$ C., preferably about $0°$ C.-$80°$ C. The amount of the compound $R^{2a}-X^1$ to be used is about 1-2 equivalents, preferably about 1-1.5 equivalents to the compound (XXIV).

In case where the compound $R^{2a}-X^1$ is gaseous, the reaction can be conducted by introducing an excess amount of the compound into the reaction mixture. Thus obtained compound (XI') can be isolated by a known method, or can be used as a starting material for the next step in the form of a reaction mixture without isolation.

3-Nitro compounds (XI) having a substituted oxy group in the ring A or B can be prepared, for example, by the following reaction scheme.

Method I

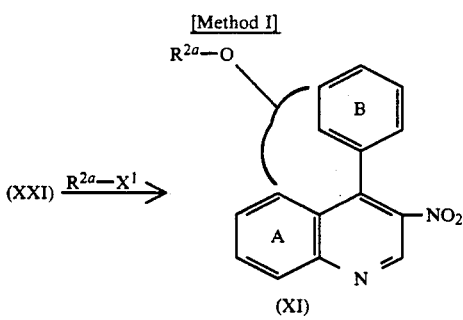

, wherein

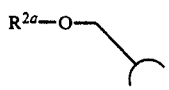

means a presence of substituent(s) $R^{2a}$—O— in the ring A or (and) B, and the other symbols have the same meanings as defined above.

Method I

The intermediate (XXI) obtained in the Method H is reacted with a compound of the formula $R^{2a}$—$X^1$ to give a compound (XI). The reaction of the intermediate (XXI) with a compound of the formula $R^{2a}$—$X^1$ can be carried out in a similar manner to the reaction of a compound (XXIV) with a compound of the formula $R^{2a}$—$X^1$ in the above Method H. Thus obtained compound (XI) can be used as a starting material in the next step in the form of a reaction mixture without isolation, though it can be isolated by a known method.

Compounds (XI) can be directly prepared by the following method in which nitroenamine (XXV) is used instead of methazonic acid in the Method E.

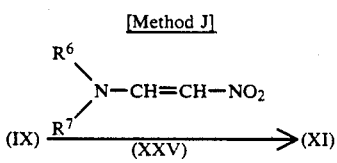

, wherein $R^6$ and $R^7$ are, the same or different, lower alkyl group, phenyl group or benzyl group, or $R^6$ and $R^7$ are combined to form a ring with the adjacent nitrogen atom.

Method J

Suitable lower alkyl group for $R^6$ and $R^7$ is the one of 1-4 carbon atoms such as methyl, ethyl, propyl, isopropyl or butyl. When $R^6$ and $R^7$ are combined to form a ring with the adjacent nitrogen atom, the ring can contain an oxygen atom. For example, the ring can be the one of 5-7 members such as pyrrolidine ring, piperidine ring, homopiperidine ring or morpholine ring.

The reaction of a compound (IX) with a compound (XXV) is usually carried out in a solvent in the presence of an acid. Ethyl acetate, acetone, benzene, toluene, etc. can be used as the solvent, and hydrochloric acid, hydrobromic acid, benzenesulfonic acid, p-toluenesulfonic acid, methanesulfonic acid, etc. can be used as the acid. The acid can be used as an anhydrous one or as an aqueous solution. The reaction can be carried out in a homogeneous system or in two layer system of the solvent and water. The amount of the compound (XXV) to be used is about 1-10 mols, preferably about 2-6 mols for one mol of the compound (IX). And the amount of the acid to be used is about 1-20 mols, preferably about 2-10 mols for one mole of the compound (IX). The reaction temperature is usually about 20° C.-100° C., preferably about 50° C.-80° C.

The compounds (XIX) can be directly prepared by the following method, in which a compound (XXVI) is used instead of the compound (XVI) in the Method G.

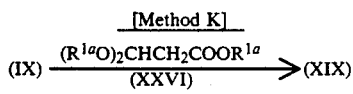

, wherein the symbol has the same meaning as defined above.

Method K

This reaction is usually carried out in a solvent such as benzene, toluene or xylene in the presence of an acid catalyst such as benzenesulfonic acid or p-toluenesulfonic acid. The amount of the compound (XXVI) to be used is usually 1-5 mols, preferablly about 1-3 mols for one mol of the compound (IX), and the amount of the acid to be used is about 0.01-1 mol, preferably about 0.05-0.5 mol for one mol of the compound (IX). The reaction is usually carried out at a temperature of around the boiling point of the solvent to be used, and preferably conducted with removing the water produced during the reaction.

Compounds (XXVIII) can be prepared by using a compound (XXVII) instead of the compound (XXVI) in the Method K, and the compound (XXVIII) can be converted to a compound (II) through a compound (XXIX) (Method L).

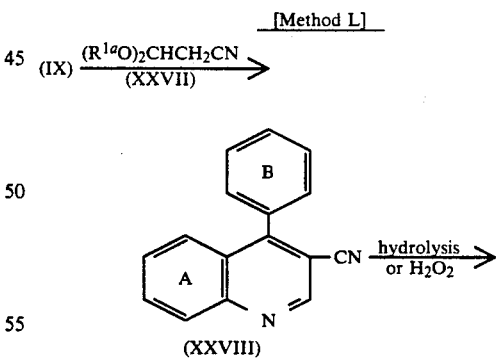

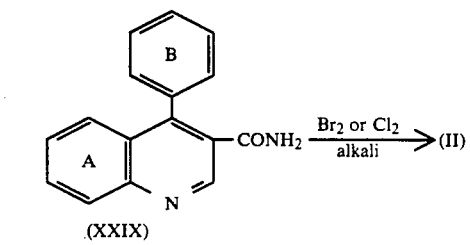

, wherein the symbols have the same meanings as above.

Method L

The reaction of a compound (IX) with a compound (XXVII) can be carried out in a similar manner to the reaction of a compound (IX) with a compound (XXVI) in the Method J. Then the compound (XXVIII) is partially hydrolized to give a compound (XXIX). The hydrolysis reaction can be carried out by using an acid or an alkali. Hydrochloric acid, hydrobromic acid, sulfuric acid, etc. is used as an acid, and sodium hydroxide, potassium hydroxide, etc. is used as an alkali. The reaction is carried out in the presence of a suitable solvent (e.g. methanol, ethanol, propanol, dioxane, dimethoxyethane, etc.) or in the absence of the solvent. The reaction temperature is about 0° C.–100° C., preferably about 20° C.–80° C.

Alternatively, the compound (XXVIII) can be converted to a compound (XXIX) by oxidation with hydrogen peroxide in the presence of an alkali. This reaction is usually carried out in a solvent similar to the one used in the hydrolysis reaction, in the presence of an alkali such as sodium hydroxide, potassium hydroxide, etc. The amounts of the alkali and hydrogen peroxide to be used are about 1-10 mols, preferably about 1.5-5 mols for one mol of the compound (XXVIII), respectively, and the reaction temperature is about 10° C.–100° C., preferably about 20° C.–80° C.

Then the compound (XXIX) is reacted with bromine or chlorine in the presence of an alkali, namely, by the so-called Hofmann reaction to give a compound (II). This reaction is carried out by reacting a compound (XXIX) with bromine or chlorine in a solvent in the presence of an alkali. Dioxane, dimethoxyethane, methanol, ethanol, etc. can be used as the solvent, and sodium hydroxide, potassium hydroxide, etc. can be used as the alkali. The reaction can be conducted by adding bromine or chlorine to a mixture of the compound (XXIX) and the alkali, or alternatively by reacting the alkali with bromine or chlorine and then reacting the produced hypobromous or hypochlorous acid with the compound (XXIX). The reaction temperature is usually about $-10°$ C.–100° C., preferably about 0° C.–80° C. When the reaction temperature is low, isocyanato compound (VI) is first produced and then it is hydrolized to give a compound (II). Accordingly, it is generally favorable to carry out the reaction step by step, namely, to carry out the reaction first at about 0° C.–20° C. and then raise the reaction temperature properly. The amount of the alkali to be used in this reaction is about 2-8 mols, preferably about 4-6 mols for one mol of the compound (XXIX), and the amount of the bromine or chlorine to be used is about 1-3 mols, preferably about 1-1.5 mols for one mol of the compound (XXIX).

Favorable examples of the compound (II) include a compound of the formula:

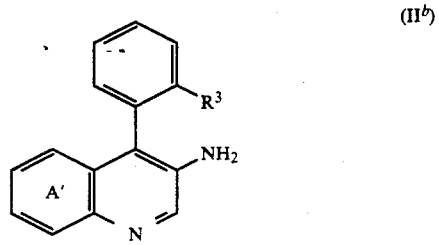

(II$^b$)

wherein $R^3$ is as defined above and the ring A' has two substituents selected from a group consisting of a halogen atom and an alkyl group having 1 to 4 carbon atoms, or a salt thereof.

In the definition of $R^3$ and the substituents on the ring A', the halogen and the alkyl group and their positions on the ring A' can be as mentioned above in relation to the symbols $R^2$, $R^3$, $R^4$ and $R^5$ of the compounds (I$^a$) and (I$^b$).

The intermediate (XXVIII) in the Method L can be hydrolyzed to give a compound (IV) by the following method.

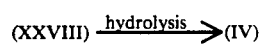

[Method M]]

Method M

This hydrolysis reaction can be carried out by using an acid or alkali in a solvent, and preferably it is conducted by using an alkali. Methanol, ethanol, propanol, 2-propanol, 2-methoxyethanol, etc. can be used as the solvent, and sodium hydroxide, potassium hydroxide, etc. can be used as the alkali. The amount of the alkali to be used is usually about 2-20 mols, preferably about 3-10 mols for one mol of the compound (XXVIII). The reaction is usually carried out at about 60° C.–150° C., preferably at about 80° C.–130° C.

The starting material (IX) in the above Method E can be prepared by a method described in Journal of Organic Chemistry, Vol. 26, page 4488(1961), ibid. Vol. 27, page 3781 (1962), etc. or by a method similar thereto. And the starting material (XV) in the Method F can be prepared, for instance, by the method described in U.S. Pat. No. 3,798,226, Yakugaku Zasshi, Vol. 93, page 1263 (1973), etc. or by a method similar thereto.

Further, the starting materials (XXV) in the Method J can be prepared, for instance, by the method described in Synthesis, page 260 (1982) or by a method similar thereto.

Activity

Pharmacological test data showing the excellent utility of the quinoline derivatives (I) and their salts of the present invention are shown in the following.

1. Acyl-CoA : cholesterol acyltransferase (ACAT) inhibitory activity.

Method

The enzyme ACAT was prepared by the method of Heider et al. described in Journal of Lipid Research, Vol. 24, page 1127 (1982), from the mucosal microsome fraction of the small intestine of male, 6-week old Sprague-Dawley rats which had been fasted for 20 hours.

ACAT activity was calculated by the method of Helgerud et al. described in Journal of Lipid Research, Vol. 22, page 271 (1981), namely, by measuring the amount of the labeled cholesterol ester produced from [1-$^{14}$C] oleoyl-CoA and endogenous cholesterol.

Results

Inhibition rates (%) of the production of the labeled cholesterol ester wherein $10^{-6}$M–$10^{-8}$M of test compounds were added are shown as an index of ACAT inhibitory activity in Table 1.

TABLE 1

| Test Compound (Example No.) | Concentration (M) | ACAT Inhibition Rate (%) |
|---|---|---|
| 1 | $10^{-6}$ | 88.3 |
| 4 | $10^{-6}$ | 75.0 |
| 11 | $10^{-6}$ | 85.5 |
| 13 | $10^{-6}$ | 84.5 |
| 14 | $10^{-6}$ | 90.1 |
| 15 | $10^{-6}$ | 91.6 |
| 17 | $10^{-6}$ | 90.1 |
| 18 | $10^{-6}$ | 85.9 |
| 21 | $10^{-6}$ | 91.8 |
| 22 | $10^{-6}$ | 96.8 |
| 23 | $10^{-6}$ | 98.0 |
| 23 | $10^{-7}$ | 94.1 |
| 23 | $10^{-8}$ | 34.3 |
| 24 | $10^{-6}$ | 88.5 |
| 25 | $10^{-6}$ | 77.0 |
| 26 | $10^{-6}$ | 87.4 |
| 27 | $10^{-6}$ | 97.2 |
| 28 | $10^{-6}$ | 92.7 |
| 29 | $10^{-6}$ | 98.2 |
| 30 | $10^{-6}$ | 98.5 |
| 31 | $10^{-6}$ | 96.9 |
| 32 | $10^{-6}$ | 98.9 |
| 32 | $10^{-8}$ | 52.1 |
| 33 | $10^{-6}$ | 99.2 |
| 34 | $10^{-6}$ | 99.3 |
| 35 | $10^{-6}$ | 97.0 |
| 36 | $10^{-6}$ | 95.6 |
| 37 | $10^{-6}$ | 87.8 |
| 38 | $10^{-6}$ | 98.3 |
| 39 | $10^{-6}$ | 98.5 |
| 39 | $10^{-8}$ | 43.3 |
| 46 | $10^{-6}$ | 75.7 |
| 50 | $10^{-6}$ | 96.8 |
| 51 | $10^{-6}$ | 97.2 |
| 52 | $10^{-6}$ | 97.9 |
| 53 | $10^{-6}$ | 85.7 |
| 54 | $10^{-6}$ | 80.7 |
| 55 | $10^{-6}$ | 97.6 |
| 58 | $10^{-6}$ | 88.5 |
| 59 | $10^{-6}$ | 97.5 |
| 60 | $10^{-6}$ | 95.1 |
| 62 | $10^{-6}$ | 97.3 |
| 63 | $10^{-6}$ | 94.4 |
| 64 | $10^{-6}$ | 69.7 |
| 67 | $10^{-6}$ | 90.1 |
| 68 | $10^{-6}$ | 98.0 |
| 69 | $10^{-6}$ | 78.2 |
| 70 | $10^{-6}$ | 97.9 |
| 71 | $10^{-6}$ | 98.0 |
| 72 | $10^{-6}$ | 97.3 |
| 73 | $10^{-6}$ | 99.6 |
| 74 | $10^{-6}$ | 99.3 |
| 75 | $10^{-6}$ | 61.2 |
| 77 | $10^{-6}$ | 96.2 |
| 78 | $10^{-6}$ | 98.2 |
| 79 | $10^{-6}$ | 79.9 |
| 80 | $10^{-6}$ | 95.9 |
| 81 | $10^{-6}$ | 97.9 |
| 83 | $10^{-6}$ | 87.3 |
| Compound B* | $10^{-6}$ | 54.5 |

*Compound B: 6-chloro-3-[3-(4-chlorophenyl)ureido]-4-phenylquinoline (U.S. Pat. No. 3,862,152, obtained in Claim 14)

It is clearly proved through the above Table 1 that the quinoline derivatives (I) including the Compound B and their salts possess excellent ACAT inhibitory activities.

2. Plasma cholesterol lowering activity in cholesterol fed rat.

1% Cholesterol diet (containing 0.5% of cholic acid and 5% of olive oil) was fed to 7-week old, male Sarague Dawley rats for 3 days. The rats were grouped by the plasma cholesterol level, and fed by the same diet containing 0.0005% of a test compound for 4 days. Blood was collected from rats during 8:30–10:00 am at the fed state, and the plasma cholesterol level was measured enzymatically. The amount of a test compound consumed by rats was calculated on the basis of the amount of the diet consumed by the rats.

Results

Plasma cholesterol level in cholesterol fed rats were significantly lowered by the test compounds as shown in Table 2.

TABLE 2

| Test Compounds (Example No.) | Dose (mg/kg/day) | Plasma Cholesterol (mg/dl) |
|---|---|---|
| Control | 0 | 240 ± 85 |
| 23 | 0.40 ± 0.03 | 126 ± 33* |
| 30 | 0.45 ± 0.02 | 143 ± 21* |
| 32 | 0.43 ± 0.04 | 119 ± 46* |

The values are mean values ± standard deviations.
*$p < 0.05$ (t - test vs control group)

It is proved by the above Table 2 that the quinoline derivatives (I) and their salts possess excellent activity for lowering plasma cholesterol.

EXAMPLES

This invention is explained in more detail by the following Reference Examples and Examples. But, it should be noted that this invention is not restricted by these Examples.

In the Reference Examples and Examples, elution of a column chromatography was conducted by observing thin layer chromatography (TLC). The observation of TLC was carried out by using silica gel 60F$_{254}$ manufactured by Merck Co. Inc. as a TLC plate and the same solvent as the one used for an eluting solvent in the column chromatography as a developing solvent, and with an UV detector as a detecting means. Silica gel 60 (70-230 mesh) manufactured by Merck Co. Inc. was used as silica gel for the column chromatography.

Abbreviations used in the Examples and Reference Examples have the following meanings.

mg: milligram, g: gram, ml: milliliter,
m.p.: melting point.

Further, room temperature means 15°-25° C.

EXAMPLE 1

2,4-Difluorophenyl isocyanate (0.24 ml) was added to a solution of 3-amino-6-chloro-4-phenylquinoline (509 mg) in anhydrous tetrahydrofuran (8 ml), and the mixture was allowed to stand at room temperature for 20 hrs. The precipitated crystals were collected by filtration. The filtrate was concentrated and the precipitated crystals were collected by filtration. Thus obtained crystals were combined and recrystallized from ethanol to give 6-chloro-3-[3-(2,4-difluorophenyl)ureido]-4-phenylquinoline as colorless crystals (638 mg, 77.8 %). m.p. 206°14 207° C.

Elemental analysis for $C_{22}H_{14}ClF_2N_3O$: Calculated: C, 64.48; H, 3.44; N, 10.25. Found C, 64.23; H, 3.55; N, 10.04.

Object compounds of the following Examples 2 to 39 were obtained by reacting a corresponding 3-aminoquinoline derivative and isocyanate in a similar manner to the above Example 1.

EXAMPLE 2

6-Chloro-3-[3-(4-fluorophenyl)ureido]-4-phenylquinoline: m.p. 205-207° C. (recrystallized from ethanol). Yield 66.5%.

Elemental analysis for $C_{22}H_{15}ClFN_3O$: Calculated: C, 67.44; H, 3.86; N, 10.72. Found: C, 67.63; H, 3.87; N, 10.76.

EXAMPLE 3

6-Chloro-3-[3-(3-fluorophenyl)ureido]-4-phenylquinoline: m.p. 213°–214° C. (recrystallized from acetone). Yield 84.1%.

Elemental analysis for $C_{22}H_{15}ClFN_3O$: Calculated: C, 67.44; H, 3.86; N, 10.72. Found: C, 67.51; H, 3.86; N, 10.64.

EXAMPLE 4

6-Chloro-3-[3-(2-fluorophenyl)ureido]-4-phenylquinoline: m.p 197°–198° C. (recrystallized from a mixture of acetone and hexane). Yield 77.3%.

Elemental analysis for $C_{22}H_{15}ClFN_3O$: Calculated: C, 67.44; H, 3.86; N, 10.72. Found: C, 67.32; H, 3.86; N, 10.70.

EXAMPLE 5

6-Chloro-3-[3-(3-methylphenyl)ureido]-4-phenylquinoline: m.p. 204°–206° C. (recrystallized from a mixture of acetone and ethanol). Yield 78.2%.

Elemental analysis for $C_{23}H_{18}ClN_3O$. Calculated: C, 71.22; H, 4.68; N, 10.83. Found C: 71.16; H, 4.67; N, 10.89.

EXAMPLE 6

6-Chloro-4phenyl-3-[3-(3-trifluoromethylphenyl)ureido]quinoline: m.p. 203°–204° C. (recrystallized from a mixture of acetone and diisopropyl ether). Yield 80.5%.

Elemental analysis for $C_{23}H_{15}ClF_3N_3O$: Calculated: C, 62.52; H, 3.42; N, 9.51. Found: C, 62.73; H, 3.71; N, 9.23.

EXAMPLE 7

6-Chloro-3-[3-(2,4-dimethoxyphenyl)ureido]-4-phenylquinoline: m.p. 210°–211° C. (recrystallized from a mixture of acetone and ethanol). Yield 41.5%.

Elemental analysis for $C_{24}H_{20}ClN_3O_3$: Calculated: C, 66.44; H, 4.65; N, 9.68. Found C, 66.38; H, 4.55; N, 9.63.

EXAMPLE 8

6-Chloro-3-[3-(3,4-dichlorophenyl)ureido]-4-phenylquinoline: m.p. 226°–227° C. (recrystallized from acetone). Yield 79.3%.

Elemental analysis for $C_{22}H_{14}Cl_3N_3O$: Calculated: C, 59.68; H, 3.19; N, 9.49. Found: C, 59.63; H, 3.07; N, 9.55.

EXAMPLE 9

6-Chloro-3-[3-(2,5-dichlorophenyl)ureido]-4-phenylquinoline (acetone solvate): m.p. 191°–192° C. (recrystallized from a mixture of acetone and diisopropyl ether). Yield 82.8%.

Elemental analysis for $C_{22}H_{14}Cl_3N_3O \cdot C_3H_6O$: Calculated: C, 59.96; H, 4.03; N, 8.39. Found C, 60.04; H, 4.04; N, 8.42.

EXAMPLE 10

6-Chloro-3-[3-(2,4-dichlorophenyl)ureido]-4-phenylquinoline: m.p. 214°–215° C. (recrystallized from acetone). Yield 74.2%.

Elemental analysis for $C_{22}H_{14}Cl_3N_3O$: Calculated: C, 59.68; H, 3.19; N, 9.49. Found: C, 59.53; H, 3.10; N, 9.45.

EXAMPLE 11

6-Bromo-3-[3-(2,4-difluorophenyl)ureido]-4-phenylquinoline: m.p. 195°–197° C. (recrystallized from a mixture of acetone and diisopropylether). Yield 82.1%.

Elemental analysis for $C_{22}H_{14}BrF_2N_3O$: Calculated: C, 58.17; H, 3.11; N, 9.25. Found: C, 57.96; H, 3.06; N, 9.11.

EXAMPLE 12

3-[3-(2,4-Difluorophenyl)ureido]-4-phenylquinoline (½ ethanol solvate): m.p. 193°–195° C. (recrystallized from ethanol). Yield 74.3%.

Elemental analysis for $C_{22}H_{15}F_2N_3O \cdot \tfrac{1}{2}C_2H_6O$: Calculated: C, 69.34; H, 4.55; N, 10.55. Found: C, 69.48; H, 4.55; N, 10.57.

EXAMPLE 13

3-[3-(2,4-Difluorophenyl)ureido]-6-methyl-4-phenylquinoline: m.p. 189°–191° C. (recrystallized from a mixture of acetone and diisopropyl ether). Yield 72.0%.

Elemental analysis for $C_{23}H_{17}F_2N_3O$: Calculated: C, 70.94; H, 4.40; N, 10.79. Found: C, 70.88; H, 4.39; N, 10.80.

EXAMPLE 14

3-[3-(2,4-Difluorophenyl)ureido]-6-ethyl-4-phenylquinoline: m.p. 189°–190° C. (recrystallized from ethanol). Yield 70.5%.

Elemental analysis for $C_{24}H_{19}F_2N_3O$: Calculated: C, 71.45; H, 4.75; N, 10.42. Found: C, 71.28; H, 4.78; N, 10.29.

EXAMPLE 15

3-[3-(2,4-Difluorophenyl)ureido]-6-isopropyl-4-phenylquinoline: m.p. 211°–212° C. (recrystallized from ethanol). Yield 74.5%.

Elemental analysis for $C_{25}H_{21}F_2N_3O$: Calculated: C, 71.93; H, 5.07; N, 10.07. Found: C, 71.92; H, 5.04; N, 9.99.

EXAMPLE 16

3-[3-(2,4-Difluorophenyl)ureido]-7-methyl-4-phenylquinoline: m.p. 195°–197° C. (recrystallized from acetone). Yield 76.2%.

Elemental analysis for $C_{23}H_{17}F_2N_3O$: Calculated: C, 70.94; H, 4.40; N, 10.79. Found: C, 70.99; H, 4.38; N, 10.67.

EXAMPLE 17

3-[3-(2,4-Difluorophenyl)ureido]-4-phenyl-6-trifluoromethylquinoline: m.p. 203°–204° C. (recrystallized from ethanol). Yield 65.3%.

Elemental analysis for $C_{23}H_{14}F_5N_3O$: Calculated: C, 62.31; H, 3.19; N, 9.48. Found: C, 62.39; H, 3.12; N, 9.52.

EXAMPLE 18

3-[3-(2,4-Difluorophenyl)ureido]-6-methoxy-4-phenylquinoline: m.p. 126°–130° C. (recrystallized from a mixture of acetone and diisopropyl ether). Yield 87.7%.

Elemental analysis for $C_{23}H_{17}F_2N_3O$: Calculated: C, 68.14; H, 4.23; N, 10.37. Found: C, 68.20; H, 4.18; N, 10.19.

EXAMPLE 19

3-[3-(2,4-Difluorophenyl)ureido]-6,7-dimethoxy-4-phenylquinoline: m.p. 202°–203° C. (recrystallized from methanol). Yield 77.2%.

Elemental analysis for $C_{24}H_{19}F_2N_3O$: Calculated: C, 66.20; H, 4.40; N, 9.65. Found: C, 65.92; H, 4.35; N, 9.49.

EXAMPLE 20

3-[3-(2,4-Difluorophenyl)ureido]-6-nitro-4-phenylquinoline (⅔ acetone solvate): m.p. 193°–194° C. (recrystallized from acetone). Yield 76.3%.

Elemental analysis for $C_{22}H_{14}F_2N_4O_3 \cdot \tfrac{2}{3} C_3H_6O$: Calculated: C, 62.79; H, 3.95; N, 12.20. Found C, 62.84; H, 4.05; N, 12.09.

EXAMPLE 21

4-(2-Chlorophenyl)-3-[3-(2,4-difluorophenyl)ureido]quinoline (¼ ethanol solvate): m.p. 198°–200° C. (recrystallized from ethanol). Yield 85.5%. Elemental analysis for $C_{22}H_{14}ClF_2N_3O \cdot \tfrac{1}{4} C_2H_6O$: Calculated: C, 63.82; H, 3.96; N, 9.71. Found: C, 63.57; H, 4.02; N, 9.64.

EXAMPLE 22

6-Chloro-3-[3-(2,4-difluorophenyl)ureido]-4-(2-fluorophenyl)quinoline: m.p. 218°–220° C. (recrystallized from ethanol). Yield 78.3%.

Elemental analysis for $C_{22}H_{13}ClF_3N_3O$: Calculated: C, 61.77; H, 3.06; N, 9.82. Found: C, 61.51; H, 3.03; N, 9.64.

EXAMPLE 23

6-Chloro-4-(2-chlorophenyl)-3-[3-(2,4-difluorophenyl) ureido]quinoline: m.p. 210°–212° C. (recrystallized from a mixture of acetone and water). Yield 86.7%.

Elemental analysis for $C_{22}H_{13}Cl_2F_2N_3O$: Calculated: C, 59.48; H, 2.95; N, 9.46. Found: C, 59.28; H, 2.88; N, 9.37.

EXAMPLE 24

6-Chloro-4-(3-chlorophenyl)-3-[3-(2,4-difluorophenyl) ureido]quinoline: m.p. 207°–208° C. (recrystallized from a mixture of acetone and water). Yield 68.1%.

Elemental analysis for $C_{22}H_{13}Cl_2F_2N_3O$: Calculated: C, 59.48; H, 2.95; N, 9.46. Found: C, 59.31; H, 2.96; N, 9.59.

EXAMPLE 25

6-Chloro-4-(4-chlorophenyl)-3-[3-(2,4-difluorophenyl) ureido]quinoline: m.p. 215°–217° C. (recrystallized from ethanol). Yield 74.1%.

Elemental analysis for $C_{22}H_{13}Cl_2F_2N_3O$: Calculated: C, 59.48; H, 2.95; N, 9.46. Found: C, 59.31; H, 2.96; N, 9.59.

EXAMPLE 26

6-Chloro-3-[3-(2,4-difluorophenyl)ureido]-4-(4-methylpheynyl)quinoline: m.p. 188°–189° C. (recrystallized from ethanol). Yield 79.7%.

Elemental analysis for $C_{23}H_{16}ClF_2N_3O$: Calculated: C, 65.18; H, 3.80; N, 9.9. Found: C, 65.19; H, 3.78; N, 9.79.

EXAMPLE 27

6-Chloro-3-[3-(2,4-difluorophenyl)ureido]-4-(2-methylphenyl)quinoline: m.p. 219°–220° C. (recrystallized from a mixture of acetone and hexane). Yield 72.6%.

Elemental analysis for $C_{23}H_{16}ClF_2N_3O_2$: Calculated: C, 65.18; H, 3.80; N, 9.91. Found: C, 65.34; H, 3.79; N, 10.04.

EXAMPLE 28

6-Chloro-3-[3-(2,4-difluorophenyl)ureido]-4-(4-methoxyphenyl)quinoline: m.p. 208°–209° C. (recrystallized from ethanol). Yield 82.7%.

Elemental analysis for $C_{23}H_{16}ClF_2N_3O_2$: Calculated: C, 62.81; H, 3.67; N, 9.55. Found: C, 62.86; H, 3.70; N, 9.50.

EXAMPLE 29

4(2-Chloro-3-[3-(2,4-difluorophenyl)ureido]-4-(2-methoxyphenyl)quinoline: m.p. 221°–222° C. (recrystallized from ethanol). Yield 65.9%. Elemental analysis for $C_{23}H_{16}ClF_2N_3O_2$: Calculated: C, 62.81; H, 3.67; N, 9.55. Found: C, 62 81; H, 3.71; N, 9.81.

EXAMPLE 30

4-(2-Chlorophenyl)-3-[3-(2,4-difluorophenyl)ureido]-6-methylquinoline: m.p. 225°–226° C. (recrystallized from acetone). Yield 64.7%.

Elemental analysis for $C_{23}H_{16}ClF_2N_3O$: Calculated: C, 65.18; H, 3.80; N, 9.91. Found: C, 65.12; H, 3.77; N, 9.87.

EXAMPLE 31

3-[3-(2,4-Difluorophenyl)ureido]-6-methyl-4-(2-methylphenyl)quinoline: m.p. 218°–220° C. (recrystallized from a mixture of acetone and benzene). Yield 65.7%.

Elemental analysis for $C_{24}H_{19}F_2N_3O$: Calculated: C, 71.45; H, 4.75; N, 10.42. Found: C, 71.26; H, 4.65; N, 10.30.

EXAMPLE 32

4-(2-Chlorophenyl)-3-[3-(2,4-difluorophenyl)ureido]-6,8-dimethylquinoline: m.p. 198°–200° C. (recrystallized from a mixture of acetone and benzene). Yield 61.4%.

Elemental analysis for $C_{24}H_{18}ClF_2N_3O$: Calculated: C, 65.83; H, 4.14; N, 9.60. Found: C, 65.67; H, 4.13; N, 9.71.

EXAMPLE 33

4-(2-Chlorophenyl)-3-[3-(2,4-difluorophenyl)ureido]-6-ethylquinoline: m.p. 228°–229° C. (recrystallized from acetone). Yield 75.4%.

Elemental analysis for $C_{24}H_{18}ClF_2N_3O$: Calculated: C, 65.83; H, 4.14; N, 9.60. Found: C, 65.80; H, 4.14; N, 9.61.

EXAMPLE 34

4-(2-Chlorophenyl)-3-[3-(2,4-difluorophenyl)ureido]-6-isopropylquinoline: m.p. 232°–233° C. (recrystallized from acetone). Yield 79.3%.

Elemental analysis for $C_{25}H_{20}ClF_2N_3O$: Calculated: C, 66.45; H, 4.46; N, 9.30. Found: C, 66.34; H, 4.45; N, 9.30.

EXAMPLE 35

6-Butyl-4-(2-chlorophenyl)-3-[3-(2,4-difluorophenyl) ureido]quinoline: m.p. 202°–203° C. (recrystallized from a mixture of acetone and hexane). Yield 72.7%.

Elemental analysis for $C_{26}H_{22}ClF_2N_3O$: Calculated: C, 67.02; H, 4.76; N, 9.02. Found: C, 66.98; H, 4.72; N, 8.78.

EXAMPLE 36

4-(2-Chlorophenyl)-3-[3-(2,4-difluorophenyl)ureido]-6-fluoroquinoline: m.p. 212°–213° C. (recrystallized from a mixture of acetone and hexane). Yield 68.3%.

Elemental analysis for $C_{22}H_{13}ClF_3N_3O$: Calculated: C, 61.77; H, 3.06; N, 9.82. Found: C, 61.74; H, 3.06; N, 9.68.

EXAMPLE 37

3-[3-(2,4-Difluorophenyl)ureido]-6-methylthio-4-phenylquinoline: m.p. 117°–120° C. (recrystallized from methanol). Yield 89.4%.

Elemental analysis for $C_{23}H_{17}F_2N_3OS$: Calculated: C, 65.55; H, 4.07; N, 9.97. Found: C, 65.43; H, 4.02; N, 9.91.

EXAMPLE 38

6-Chloro-4-(2-chlorophenyl)-3-[3-(2,4-difluorophenyl) ureido]-8-methylquinoline: m.p. 199°–201° C. (recrystallized from a mixture of acetone and benzene). Yield 67.8%.

Elemental analysis for $C_{23}H_{15}Cl_2F_2N_3O$: Calculated: C, 60.28; H, 3.30; N, 9.17. Found: C, 60.25; H, 3.30; N, 9.04.

EXAMPLE 39

3-[3-(2,4-Difluorophenyl)ureido]-6,8-dimethyl-4-(2-methylphenyl)quinoline (½ ethanol solvate): m.p. 200°–201° C. (recrystallized from ethanol). Yield 66.0%.

Elemental analysis for $C_{25}H_{21}F_2N_3O \cdot \tfrac{1}{2}C_2H_6O$: Calculated: C, 70.89; H, 5.49; N, 9.54. Found: C, 70.63; H, 5.41; N, 9.46.

EXAMPLE 40

A mixture of 6-chloro-3-methylamino-4-phenylquinoline (0.54 g), 2,4-difluorophenyl isocyanate (0.48 ml) and anhydrous toluene (10 ml) was refluxed for 22 hrs. and then concentrated. The residue was purified by a column chromatography on silica gel and recrystallized from a mixture of ethyl acetate and ethanol to give 6-chloro-3-[3-(2,4-difluorophenyl)-1-methylureido]-4-phenylquinoline as colorless crystals. Yield 0.56 g (66%). m.p. 200°–201° C.

Elemental analysis for $C_{23}H_{16}ClF_2N_3O$: Calculated: C, 65.18; H, 3.80; N, 9.91. Found: C, 65.24; H, 3.70; N, 9.81.

The compounds of the following Examples 41–44 were obtained in a manner similar to that described in Example 40.

EXAMPLE 41

6-Chloro-3-[3-(2,4-difluorophenyl)-1-ethylureido]-4-phenylquinoline: m.p. 141°–142° C. (recrystallized from ethanol). Yield 53.7%.

Elemental analysis for $C_{24}H_{18}ClF_2N_3O$: Calculated: C, 65.83; H, 4.14; N, 9.60. Found: C, 65.73; H, 4.22; N, 9.68.

EXAMPLE 42

3-(1-Butyl-3-(2,4-difluorophenyl)ureido]-6-chloro-4-phenylquinoline: m.p. 66°–69° C. (recrystallized from a mixture of ethyl ether and hexane). Yield 59.5%.

Elemental analysis for $C_{26}H_{22}ClF_2N_3O$: Calculated: C, 67.02; H, 4.76; N, 9.02. Found: C, 67.06; H, 4.85; N, 8.99.

EXAMPLE 43

3-[1-Benzyl-3-(2,4-difluorophenyl)ureido]-6-chlorophenylquinoline: m.p. 150°–152° C. (recrystallized from ethanol). Yield 47%.

Elemental analysis for $C_{29}H_{20}ClF_2N_3O$: Calculated: C, 69.67; H, 4.03; N, 8.40. Found: C, 69.66; H, 4.10; N, 8.25.

EXAMPLE 44

6-Chloro-3-[3-(2,4-difluorophenyl)-1-heptylureido]4-phenylquinoline: m.p. 109°–110° C. (recrystallized from ethanol). Yield 29.7%.

Elemental analysis for $C_{29}H_{28}ClF_2N_3O$: Calculated: C, 68.57; H, 5.56; N, 8.27. Found: C, 68.67; H, 5.55; N, 8.05.

EXAMPLE 45

A 10% solution (1.5 ml) of trichloromethyl chloroformate in toluene was added dropwise under stirring to a mixture of 353 mg of 6-chloro-3-heptylamino-4-phenylquinoline, 8 mg of activated charcoal, 0.14 ml of triethylamine and 6 ml of anhydrous tetrahydrofuran. After the mixture was stirred at room temperature overnight, nitrogen gas was introduced into the mixture to remove excess phosgene. Then, to the mixture were added a solution of p-chloroaniline (126 mg) in 6 ml of anhydrous tetrahydrofuran, 0.28 ml of triethylamine and 24 mg of 4-dimethylaminopyridine, and the mixture was refluxed for 12 hrs. The resultant precipitate was removed by filtration, and the filtrate was concentrated. The residue was recrystallized from ethanol to give 6-chloro-3-[3-(4-chlorophenyl)-1-heptylureido]-4-phenylquinoilne as colorless crystals.

Yield 207 mg 40.9%. m.p. 180°–382° C.

Elemental analysis for $C_{29}H_{29}Cl_2N_3O$: Calculated: C, 68.77; H, 5.77; N, 8.30. Found: C, 69.00; H, 5.80; N, 8.01.

EXAMPLE 46

Triethylamine (0.34 ml) was added to a mixture of 6-chloro-4-phenyl-3-quinolinecarboxylic acid (566 mg), diphenylphosphoryl azide (660 ml) and dioxane (10 ml). The mixture was stirred for 15 mins. at room temperature and then for 20 mins. under reflux. After cooling, 2,6-difluoroaniline (310 mg) was added to the mixture. It was stirred for 15 mins. at room temperature and then for 30 mins. under reflux. The mixture was diluted with water and extracted with ethyl acetate. The organic layer was washed with water, 1N-hydrochloric acid, water, saturated aqueous solution of sodium hydrogen carbonate and water, successively. After being dried over anhydrous magnesium sulfate, the solvent was distilled off. The residue was recrystallized to give 6-chloro-3-[3-(2,6-difluorophenyl)ureido]-4-phenylquinoline as colorless needles. Yield 562 mg (68.7%). m.p. 228°–229° C.

Elemental analysis for $C_{22}H_{14}ClF_2N_3O$: Calculated: C, 64.48; H, 3.44; N, 10.25. Found: C, 64.64; H, 3.40; N, 10.01.

EXAMPLE 47

6-Chloro-3-[3-(2,4-dimethylphenyl)ureido]-4-phenylquinoline was obtained in a manner similar to that described in Example 46. m.p. 230°–231° C. (recrystallized from acetone). Yield 42.9%.

Elemental analysis for $C_{24}H_{20}ClN_3O$: Calculated C, 71.73; H, 5.02; N, 10.46. Found C, 71.75; H, 4.96; N, 10.46.

EXAMPLE 48

6-Chloro-3-3-(2,4-difluorobenzyl)ureido]-4-phenylquinoline was obtained in a manner similar to that described in Example 46. m.p. 243°–244° C. (recrystallized from acetone). Yield 22.0%.

Elemental analysis for $C_{23}H_{16}ClF_2N_3O$: Calculated: C, 65.18; H, 3.80; N, 9.91. Found: C, 64.91; H, 3.72; N, 9.71.

EXAMPLE 49

| (1) | 4-(2-chlorophenyl)-3-[3-(2,4-difluorophenyl)ureido]-6,8-dimethylquinoline | 10 g |
| (2) | lactose | 50 g |
| (3) | cornstarch | 15 g |
| (4) | carboxymethylcellulose calcium | 44 g |
| (5) | magnesium stearate | 1 g |
| | Total | 120 g |
| | | (into 1000 tablets) |

The total amount of (1), (2) and (3) and 30 g of (4) were kneaded with water. The mixture was dried under vaccum and then made into granules. To the granule powders were mixed 14 g of (4) and 1 g of (5), and they were compressed with a tablet machine into 1000 tablets. A tablet contains 10 mg of (1).

The compounds of the following Examples 50–55 were obtained in a manner similar to that described in Example 1.

EXAMPLE 50

6-Chloro-4-(2-Chlorophenyl)-3-[3-(4-chlorophenyl)ureido]quinoline: m.p. 217°–219° C. (recrystallized from a mixture of acetone and benzene). Yield 56.8%.

Elemental analysis for $C_{22}H_{14}C_{13}N_3O$: Calculated: C, 59.68; H, 3.19; N, 9.49. Found: C, 59.47; H, 3.12; N, 9.43.

EXAMPLE 51

4-(2-Chlorophenyl)-3-[3-(4-chlorophenyl)ureido]-6,8-dimethylquinoline: m.p. 219°–221° C. (recrystallized from a mixture of acetone and benzene). Yield 61.3%.

Elemental analysis for $C_{24}H_{19}Cl_2N_3O$: Calculated: C, 66.06; H, 4.39; N, 9.63. Found: C, 65.96; H, 4.42; N, 9.50.

EXAMPLE 52

6-Chloro-3-[3-(2,4-difluorophenyl)ureido]-4-(2-methylthiophenyl)quinoline: m.p. 219°–221° C. (recrystallized from acetone). Yield 69.1%.

Elemental analysis for $C_{23}H_{16}ClF_2N_3OS$: Calculated: C, 60.59; H, 3.54; N, 9.22. Found: C, 60.75; H, 3.46; N, 9.29.

EXAMPLE 53

6-Difluoromethylthio-3-[3-(2,4-difluorophenyl)ureido]-4-phenylquinoline: m.p. 110°–112° C. (recrystallized from methanol). Yield 20.6%.

Elemental analysis for $C_{23}H_{15}F_4N_3OS$: Calculated: C, 60.39; H, 3.31; N, 9.19. Found: C, 60.44; H, 3.28; N, 9 08.

EXAMPLE 54

6-Difluoromethoxy-3-[3-(2,4-difluorophenyl)ureido]-4 4-phenylquinoline: m.p. 102°–104° C. (recrystallized from methanol). Yield 58.5%.

Elemental analysis for $C_{23}H_{15}F_4N_3O_2$: Calculated: C, 62.59; H, 3.43; N, 9.52. Found: C, 62.50; H, 3.31; N, 9.44.

EXAMPLE 55

8-Chloro-4-(2-chlorophenyl)-3-[3-(2,4-difluorophenyl) ureido]-6-methylquinoline: m.p. 220°–222° C. (recrystallized from a mixture of acetone and benzene). Yield 63.0%.

Elemental analysis for $C_{23}H_{15}Cl_2F_2N_3O$: Calculated: C, 60.28; H, 3.30; N, 9.17. Found: C, 59.98; H, 3.20; N, 9.13.

EXAMPLE 56

3-[1-Butyl-3-(2,4-difluorophenyl)ureido]-6-chloro-4-(2-chlorophenyl)quinoline was obtained in a manner similar to that described in Example 40. m.p. 63°–66° C. (recrystallized from a mixture of ethyl acetate and hexane). Yield 72.0%.

Elemental analysis for $C_{26}H_{21}Cl_2F_2N_3O$: Calculated: C, 62.41; H, 4.23; N, 8.40. Found: C, 62.37; H, 4.16; N, 8.33.

EXAMPLE 57

4-(2-Chlorophenyl)-3-[3-(2,4-difluorophenyl)ureido]-6,8-dimethylquinoline (0.2 g), obtained in Exmaple 32, was dissolved under heating at 80° C. in a mixture of acetone (10 ml) and 2N-hydrochloric acid (0.5 ml), and then the solution was concentrated. The resultant precipitate was collected by filtration to give 4-(2-chlorophenyl)-3-[3-(2,4-difluorophenyl)ureido]-6,8-dimethylquinoline hydrochloride as pale yellow needles. Yield 0.19%. m.p. 227°–228° C.

Elemental analysis for $C_{24}H_{18}ClF_2N_3O \cdot HCl$: Calculated: C, 60.77; H, 4.04; N, 8.86. Found: C, 60.92; H, 4.01; N 8.78.

The compounds of the following Examples 58–60 were obtained in a manner similar to that described in Exampel 1.

EXAMPLE 58

6-Chloro-3-[3-(4-fluoro-3-nitrophenyl)ureido]-4-(2-methylphenyl)quinoline: m.p. 229°–232° C. (recrystallized from acetone). Yield 58.0%.

Elemental analysis for $C_{23}H_{16}ClFN_4O_3$: Calculated: C, 61.27; H, 3.58; N, 12.43. Found: C, 60.99; H, 3.56; N, 12.34.

EXAMPLE 59

3-[3-(2,4-Difluorophenyl)ureido]-6-mehtyl-4-(2-mehtylthiophenyl)quinoline(methanol solvate): m.p. 213°–215° C. (recrystallized from methanol). Yield 87.0%.

Elemental analysis for $C_{24}H_{19}F_2N_3OS \cdot CH_4O$: Calculated: C, 64.22; H, 4.96; N, 8.99. Found: C, 64.27; H, 4.94; N, 9.03.

EXAMPLE 60

6-Chloro-3-[3-(2,4-difluorophenyl)ureido]-4-(3,4-dimethoxyphenyl)quinoline: m.p. 252°–254° C. (recrystallized from acetone). Yield 85.4%.

Elemental analysis for $C_{24}H_{18}ClF_2N_3O_3$: Calculated: C, 61.35; H, 3.86; N, 8.94. Found: C, 61.33; H, 3.85; N, 8.87.

EXAMPLE 61

4-(2-Chlorophenyl)-6,8-dimethyl-3-quinolinecarboxylic acid was reacted with diphenylphosphoryl azide and then with 2,4-difluoroaniline to give 4-(2-chlorophenyl)-3-[3-(2,4-difluorophenyl)ureido]-6,8- dimethylquinoline in a manner similar to that described in Example 46. Yield 35.9%. m.p. 198°-200° C.

This substance was identical with that obtained in Example 32.

EXAMPLE 62

In a similar manner as Example 46, 4-(2-chlorophenyl)-6,8-dimethyl-3-quinoinecarboxylic acid was reacted with diphenylphosphorylazide and then with 2,4,6-trifluoroaniline to give 4-(2-chlorophenyl)-6,8-dimethyl-3-[3-(2,4,6-trifluorophenyl)ureido]quinoline. m.p. 219°-220° C. (recrystallized from ethanol). Yield 73.0%.

Elemental analysis for $C_{24}H_{17}ClF_3N_3O$: Calculated: C, 63.23; H, 3.76; N, 9.22. Found: C, 63.14; H, 3.67; N, 9.08.

EXAMPLE 63

A mixture of 4-(2-chlorophenyl)-3-[3-(2,4-difluorophenyl)ureido]-6,8-dimethylquinoline (1.1 g), m-chloroperbenzoic acid (1.08 g) and dichloromethane (15 ml) was refluxed for 20 hrs. The reaction mixture was washed with aqueous sodium sulfite solution, aqueous sodium hydrogen carbonate solution and water, successively. After being dried over anhydrous magnesium sulfate, the solvent was distilled off. The residue was recrystallized from a mixture of methanol and chloroform to give 4-(2-chlorophenyl)-3-[3-(2,4-difluorophenyl)ureido]-6,8-dimethylquinoline 1-oxide as pale yellow prisms. Yield 0.72 g (63.2%). m.p. 230°-232° C.

Elemental analysis for $C_{24}H_{18}ClF_2N_3O_2$: Calculated C, 63.51; H, 4.00; N, 9.26. Found: C, 63.89; H, 3.91; N, 9.09.

EXAMPLE 64

Triethylamine (0.37 ml) was added dropwise to a mixture of 3,4,5-trimethoxybenzoic acid (563 mg), diphenylphosphoryl azide (730 mg) and dioxane (10 ml) under stirring. The mixture was further stirred for 30 mins. at room temperature and then for 40 mins. under reflux to prepare a solution of 3,4,5-trimethoxyphenyl isocyanate. After cooling, to the resultant solution was added 3-amino-4-(2-chlorophenyl)-6,8-dimethylquinoline (500 mg), and the whole was stirred at room temperature overnight. The reaction mixture was concentrated, and the residue was purified by a column chromatography on silica gel and recrystallized from dichloromethane to give 4-(2-chlorophenyl)-6,8-dimethyl-3-[3-(3,4,5-trimethoxyphenyl)ureido]-quinoline as colorless needles. Yield 490 mg (56.3%). m.p. 204°-206° C.

Elemental analysis for $C_{27}H_{26}ClN_3O_4$: Calculated: C, 65.92; H, 5.33; N, 8.54. Found: C, 65.81; H, 5.29; N, 8.47.

The compounds of the following Examples 65 and 66 were obtained in a manner similar to that described in Example 64.

EXAMPLE 65

3-[3-(3,5-Di-tert-butyl-4-hydroxyphenyl)ureido]-4-(2-chlorophenyl)ureido]-4-(2-chlorophenyl)-6,8-dimethylquinoline m.p. 262°-264° C. (recrystallized from acetone). Yield 20.6%.

Elemental analysis for $C_{32}H_{36}ClN_3O_2$: Calculated: C, 72.50; H, 6.84; N, 7.93. Found: C, 72.22; H, 6.83; N, 7.77.

EXAMPLE 66

3-[3-(3,5-Di-tert-butyl-4-hydroxyphenyl)ureido]-6-chloro-4-phenylquinoline: m.p. 277°-280° C. (recrystallized from acetone). Yield 13.2%.

Elemental analysis for $C_{30}H_{32}ClN_3O_2$: Calculated: C, 71.77; H, 6.42; N, 8.37. Found: C, 71.88; H, 6.39; N, 8.36.

EXAMPLE 67

3-[1-(3,5-Di-tert-butyl-4-hydroxybenzyl)-3-(2,4-difluorophenyl)ureido]-4-(2-chlorophenyl)-6,8-dimethylquinoline was obtained in a manner similar to that described in Example 40. m.p. 124°-126° C. (recrystallized from methanol). Yield 66.2%.

Elemental analysis for $C_{39}H_{40}ClF_2N_3O_2$: Calculated: C, 71.38; H, 6.14; N, 6.40. Found: C, 71.27; H, 6.43; N, 6.30.

EXAMPLE 68

6-Chloro-3-[3-(2,4-difluorophenyl)ureido]-4-(2,3,4-trimethoxyphenyl)quinoline was obtained in a manner similar to that described in Example 1. m.p. 120°-122° C. (recrystallized from methanol). Yield 94.9%.

Elemental analysis for $C_{25}H_{20}ClF_2N_3O_4$: Calculated: C, 60.07; H, 4.03; N, 8.41. Found: C, 59.68; H, 4.05; N, 8.30.

EXAMPLE 69

6-Chloro-3-[3-(2,4-difluorophenyl)ureido]-4-(2-hydroxy-3,4-dimethoxyphenyl)quinoline was obtained in a manner similar to that described in Example 1. m.p. 218°-220° C. (recrystallized from methanol). Yield 82.0%.

Elemental analysis for $C_{24}H_{18}ClF_2N_3O_4$: Calculated: C, 59.33; H, 3.73; N, 8.65. Found: C, 59.53; H, 3.67; N, 8.50.

The compounds of the following Examples 70 and 71 were obtained in a manner similar to that described in Example 46.

EXAMPLE 70

4-(2-Chlorophenyl)-6,8-dimethyl-3-[3-(2,6-dimethylphenyl)ureido]quinoline: m.p. 237°-238° C. (recrystallized from ethanol). Yield 56.5%.

Elemental analysis for $C_{26}H_{24}ClN_3O$: Calculated: C, 72.63; H, 5.63; N, 9.77. Found: C, 72.85; H, 5.64; N, 9.78.

EXAMPLE 71

4-(2-Chlorophenyl)-3-[3-(2,6-diisopropylphenyl)ureido]-6,8-dimethylquinoline: m.p. 257°-258° C. (recrystallized from ethanol). Yield 63.3%.

Elemental analysis for $C_{30}H_{32}ClN_3O$: Calculated: C, 74.13; H, 6.64; N, 8.65. Found: C, 74.32; H, 6.64; N, 8.62.

The compounds of the following Examples 72-75 were obtained in a manner similar to that described in Example 1.

EXAMPLE 72

4-(2-Chlorophenyl)-3-[3-(4-nitrophenyl)ureido]-6,8-dimethylquinoline: m.p. 228° C. (decomp.) (recrystallized from a mixture of acetone and hexane). Yield 51.5%.

Elemental analysis for $C_{24}H_{19}ClN_4O_3$: Calculated: C, 64.50; H, 4.29; N, 12.54. Found: C, 64.29; H, 4.18; N, 12.27.

EXAMPLE 73

4-(2-Chlorophenyl)-3-[3-(2,4-difluorophenyl)ureido]-6,7-dimethylquinoline: m.p. 220°-222° C. (recrystallized from acetone). Yield 73.8%.

Elemental analysis for $C_{24}H_{18}ClF_2N_3O$: Calculated C, 65.83; H, 4.14; N, 9.60. Found: C, 65.65; H, 4.08; N, 9.52.

EXAMPLE 74

4-(2-Chlorophenyl)-3-[3-(2,4-difluorophenyl)ureido]-6,7,8-trimethylquinoline: m.p. 197°-199° C. (recrystallized from a mixture of ethyl ether and hexane). Yield 65.6%.

Elemental analysis for $C_{25}H_{20}ClF_2N_3O$: Calculated: C, 66.45; H, 4.46; N, 9.30. Found: C, 66.41; H, 4.41; N, 9.27.

EXAMPLE 75

1.0 ml of a 1:2 (v/v) mixture of boron tribromide and dichloromethane was added at 0° C. to a solution of 6-chloro-3-[3-(2,4-difluorophenyl)ureido]-4-(3,4-dimethoxyphenyl)quinoline (250 mg) in dichloromethane (20 ml). Furthermore, the mixture was stirred at 0° C. for 30 mins., diluted with water, and then extracted with ethyl acetate. The extract was washed with water, and dried over anhydrous sulfate and distilled to remove the solvent. The residue was recrystallized from methanol to give 6-chloro-3-[3-(2,4-difluorophenylureido]-4-(3,4-dihydroxyphenyl)quinoline.½hydrate as crystals (167 mg, 70.8%). m.p. >300° C.

Elemental analysis for $C_{22}H_{14}ClF_2N_3O_3.\frac{1}{2}H_2O$: Calculated: C, 58.61; H, 3.35; N, 9.32. Found: C, 58.48; H, 3.18; N, 9.21.

EXAMPLE 76

Triethylamine (0.15 ml) was dropwise added to a mixture of 4-acetoxy-3,5-didiisopropylbenzoic acid (238 mg), diphenylphosphoryl azide (300 mg) and benzene (10 ml) under stirring. The mixture was further stirred for 30 mins. at room temperature, and for 40 mins. under reflux to prepare a solution of 4-acetoxy-3,5-diisopropylphenylisocyanate. After cooling, to the solution were added a solution of 3-amino-4-(2-chlorophenyl)-6,8-dimethylquinoline (255 mg) in benzene (255 mg) and then triethylamine (0.15 ml). The whole was stirred for 2 hrs. at room temperature, then for 3 hrs. under reflux, and thereto was added ethyl acetate. The organic layer was separated, washed with 2N-hydrochloric acid and water successively, and dried over anhydrous magnesium sulfate and then distilled to remove the solvent. The residue was recrystallized from a mixture of acetone and isopropyl ether to give 3-[3-(4-acetoxy-3,5-diisopropylphenyl)ureido]-4-(2-chlorophenyl)-6,8-dimethylquinoline as colorless needles. Yield 367 mg (74.9%). m.p. 248°-249° C.

Elemental analysis for $C_{32}H_{34}ClN_3O_3$: Calculated: C, 70.64; H, 6.30; N, 7.72. Found: C, 70.73; H, 6.57; N, 7.48.

In a similar manner as Example 76, the compounds of the following Examples 77 and 78 were obtained.

EXAMPLE 77

3-[3-(4-Acetoxy-3,5-dimethylphenyl)ureido]-4-(2-chlorophenyl)-6,8-dimethylquinoline: m.p. 179°-181° C. (recrystallized from a mixture of acetone and isopropyl ether). Yield 69.9%.

Elemental analysis for $C_{28}H_{26}ClN_3O_3$: Calculated: C, 68.92; H, 5.37; N, 8.61. Found: C, 68.90; H, 5.49; N, 8.48.

EXAMPLE 78

3-[3-(4-Acetoxy-2,3,5-trimethylphenyl)ureido]-4-(2-chlorophenyl)-6,8-dimethylquinoline: m.p. 222°-224° C. (recrystallized from a mixture of acetone and isopropyl ether). Yield 61.1%.

Elemental analysis for $C_{29}H_{28}ClN_3O_3$: Calculated C, 69.38; H, 5.62; N, 8.37. Found: C, 69.24; H, 5.62; N, 8.34.

EXAMPLE 79

A mixture of 3-[3-(4-acetoxy-3,5-diisopropylphenyl)ureido]-4-(2-chlorophenyl)-6,8-dimethylquinoline (300 mg), methanol (20 ml) and 1N-sodium hydroxide (2 ml) was stirred for 1.5 hrs. at room temperature. After concentrated, the mixture was diluted with water, acidified with 2N-hydrochloric acid and then extracted with ethyl acetate. The extract was washed with water, dried over anhydrous magnesium sulfate and then distilled to remove the solvent. The residue was recrystallized from a mixture of acetone and isopropyl ehter to give 4-(2-chlorophenyl)-3-[3-(4-hydroxy-3,5-diisopropylphenyl)ureido]-6,8-dimethylquinoline as colorless prisms. Yield 116 mg (41.9%). m.p. 194°-196° C.

Elemental analysis for $C_{30}H_{32}ClN_3O_2$: Calculated: C, 71.77; H, 6.42; N, 8.37. Found: C, 71.39; H, 6.22; N, 8.28.

In a similar manner as Example 79, the compounds of the following Examples 80 and 81 were obtained.

EXAMPLE 80

4-(2-Chlorophenyl)-3-[3-(4-hydroxy-3,5-dimethylphenyl)ureido]-6,8-dimethylquinoline: m.p. 229°-231° C. (recrystallized from a mixture of acetone and isopropyl ether). Yield 54.8%.

Elemental analysis for $C_{26}H_{24}ClN_3O_2$: Calculated: C, 70.03; H, 5.42; N, 9.42. Found: C, 69.96; H, 5.60; N, 9.29.

EXAMPLE 81

4-(2-Chlorophenyl)-3-[3-(4-hydroxy-2,3,5-trimethylphenyl)ureido]-6,8-dimethylquinoline: m.p. 244°-245° C. (recrystallized from a mixture of acetone and isopropyl ether). Yield 43.0%.

Elemental analysis for $C_{27}H_{26}ClN_3O_2$: Calculated: C, 70.50; H, 5.70; N, 9.14. Found: C, 70.51; H, 5.66; N, 9.14.

EXAMPLE 82

6-Chloro-3-[3-(2,4-difluorophenyl)ureido]-4-(2,3,4-trihydroxyphenyl)quinoline.½hydrate was obtained in a manner similar to that described in Example 75. m.p. >300° C. (recrystallized from a mixture of acetone and isopropyl ether). Yield 83.0%.

Elemental analysis for $C_{22}H_{14}ClF_2N_3O_4.\frac{1}{2}H_2O$: Calculated: C, 56.60; H, 3.24; N, 9.00. Found: C, 56.90; H, 3.02; N, 8.71.

EXAMPLE 83

4-(2-Chlorophenyl)-3-[3-(2,4-difluorophenyl)ureido]-5-methylquinoline was obtained in a manner similar to that described in Example 1. m.p. 218°-220° C. (recrystallized from ethanol). Yield 64.3%.

Elemental analysis for $C_{23}H_{16}ClF_2N_3O$: Calculated: C, 65.18; H, 3.80; N, 9.91. Found: C, 65.39; H, 3.72; N, 9.85.

REFERENCE EXAMPLE 1

(1) To a solution of 2-amino-5-trifluoromethylbenzophenone (5.3 g) in acetone (100 ml) were added 20% hydrochloric acid (40 ml) and methazonic acid (5.0 g, wet).

The mixture was allowed to stand at room temperature overnight and diluted with water. The precipitated yellow crystals were collected by filtration to give 6.4 g of 2-(2-nitrovinyl amino)-5-trifluoromethylbenzophenone (Yield 95.2%). A part of the crystals was recrystallized from acetone to give yellow needles, m.p. 196°-198° C.

Elemental analysis for $C_{16}H_{11}F_3N_2O_3$: Calculated: C, 57.15; H, 3.30; N, 8.33. Found: C, 57.16; H, 3.27; N, 8.21.

(2) 2N-Sodium hydroxide solution (9.0 ml) was added dropwise to a mixture of 2-(2-nitrovinylamino)-5-trifluoromethylbenzophenone (6.0 g) and methanol (60 ml) under stirring. After stirring further for 30 mins. at room temperature, the mixture was diluted with water to give 3-nitro-4-phenyl-6-trifluoromethylquinoline as crystals (4.88 g, 4.5 %). It was recrystallized from a mixture of chloroform and methanol to give pale yellow needles (4.50 g, 79,2 %). m.p 192°–193° C.

Elemental analysis for $C_{16}H_9F_3N_2O_2$: Calculated: C, 60.38; H, 2.85; N, 8.80. Found: C, 60.16; H, 2.82; N, 8.68.

(3) A mixture of 3-nitro-4-phenyl-6-trifluoromethylquinoline (2.0 g), stannous chloride dihydrate (5.0 g) and conc. hydrochloric acid (20 ml) was stirred for 1 hr. at 100° C. The mixture was neutralized with 6N-sodium hydroxide solution and extracted with chloroform. The chloroform layer was washed with water, dried over anhydrous magnesium sulfate, and then distilled to remove the solvent. The residue was recrystallized from a mixture of isopropyl ether and hexane to give 3-amino-4-phenyl-6-trifluoromethylquinoline (1.46 g, 80 %). m.p. 107°–108° C.

Elemental analysis for $C_{16}H_{11}F_3N_2$: Calculated: C, 66.66; H, 3.85; N, 9.72. Found: C, 66.67; H, 3.79; N, 9.49.

In a similar manner as above were obtained the compounds of the following Reference Examples 2-17.

REFERENCE EXAMPLE 2

(1) 5-Ethyl-2-(2-nitrovinylamino)benzophenone: (not isolated)

(2) 6-Ethyl-3-nitro-4-phenylquinoline: m.p. 139°–140° C.

(3) 3-Amino-6-ethyl-4-phenylquinoline: m.p. 206°–209° C.

REFERENCE EXAMPLE 3

(1) 5-Isopropyl-2-(2-nitrovinylamino)benzophenone: m.p 166°–167° C.

(2) 6-Isopropyl-3-nitro-4-phenylquinoline: m.p. 115°–116° C.

(3) 3-Amino-6-isopropyl-4-phenylquinoline: m.p. 128°–129° C.

REFERENCE EXAMPLE 4

(1) 4-Methyl-2-(2-nitrovinylamino)benzophenone: m.p. 163°–164° C.

(2) 7-Methyl-3-nitro-4-phenylquinoline: m.p. 176°–177° C.

(3) 3-Amino-7-methyl-4-phenylquinoline: m.p. 167°–168° C.

REFERENCE EXAMPLE 5

(1) 2'-Chloro-2-(2-nitrovinylamino)benzophenone: m.p. 140°–144° C.

(2) 4-(2-Chlorophenyl)-3-nitroquinoline: m.p. 124°–125° C.

(3) 3-Amino-4-(2-chlorophenyl)quinoline: m.p. 155°–156° C.

REFERENCE EXAMPLE 6

(1) 5-Chloro-2'-fluoro-2-(2-nitrovinylamino)benzophenone: m.p. 219°–221° C.

(2) 6-Chloro-4-(2-fluorophenyl)-3-nitroquinoline: m.p. 150°–151° C.

(3) 3-Amino-6-chloro-4-(2-fluorophenyl)quinoline: m.p. 150°–151° C.

REFERENCE EXAMPLE 7

(1) 5,3'-Dichloro-2-(2-nitrovinylamino)benzophenone: m.p. 195°–197° C.

(2) 6-Chloro-4-(3-chlorophenyl)-3-nitroquinoline: m.p. 135°–136° C.

(3) 3-Amino-6-chloro-4-(3-chlorophenyl)quinoline: m.p. 154°–155° C.

REFERENCE EXAMPLE 8

(1) 5,4'-Dichloro-2-(2-nitrovinylamino)benzophenone: m.p. 218°–220° C.

(2) 6-Chloro-4-(4-chlorophenyl)-3-nitroquinoline: m.p. 148°–149° C.

(3) 3-Amino-6-chloro-4-(4-chlorophenyl)quinoline: m.p 190°–191° C.

REFERENCE EXAMPLE 9

(1) 5-Chloro-4'-methyl-2-(2-nitrovinylamino)benzophenone: m.p. 227°–228° C.

(2) 6-Chloro-4-(4-methylphenyl)-3-nitroquinoline: m.p. 127°–128° C.

(3) 3-Amino-6-chloro-4-(4-methylphenyl)quinoline: m.p. 144°–145° C.

REFERENCE EXAMPLE 10

(1) 5-Chloro-2'-methyl-2-(2-nitrovinylamino)benzophenone: m.p. 184°–186° C.

(2) 6-Chloro-4-(2-methylphenyl)-3-nitroquinoline: m.p. 176°–177° C.

(3) 3-Amino-6-chloro-4-(2-methylphenyl)quinoline: m.p. 132°–133° C.

REFERENCE EXAMPLE 11

(1) 5-Chloro-2'-methoxy-2-(2-nitrovinylamino)benzophenone: m.p. 217°–218° C.

(2) 6-Chloro-4-(2-methoxyphenyl)-3-nitroquinoline: m.p. 213°–214° C.

(3) 3-Amino-6-chloro-4-(2-methoxyphenyl)quinoline: m p. 137°–138° C.

REFERENCE EXAMPLE 12

(1) 2'-Chloro-5-methyl-2-(2-nitrovinylamino)benzophenone: m.p. 136°–137° C.

(2) 4-(2-Chlorophenyl)-6-methyl-3-nitroquinoline: m p. 168°–169° C.

(3) 3-Amino-4-(2-chlorophenyl)-6-methylquinoline: m.p. 121°–123° C.

REFERENCE EXAMPLE 13

(1) 5,2'-Dimethyl-2-(2-nitrovinylamino)benzophenone: m.p. 148°–149° C.

(2) 6-Methyl-4-(2-methylphenyl)-3-nitroquinoline: m.p. 112°–113° C.

(3) 3-Amino-6-methyl-4-(2-methylphenyl)quinoline: an oil.

REFERENCE EXAMPLE 14

(1) 2'-Chloro-5-ethyl-2-(2-nitrovinylamino)benzophenone: m.p. 180°–181° C.

(2) 4-(2-Chlorophenyl)-6-ethyl-3-nitroquinoline: m.p. 151°–152° C.

(3) 3-Amino-4-(2-chlorophenyl)-6-ethylquinoline: m.p. 91°–92° C.

REFERENCE EXAMPLE 15

(1) 2'-Chloro-5-isopropyl-2-(2-nitrovinylamino)benzophenone: m.p. 166°–167° C.

(2) 4-(2-Chlorophenyl)-6-isopropyl-3-nitroquinoline: m.p. 116°-117° C.

(3) 3-Amino-4-(2-chlorophenyl)-6-isopropylquinoline: m.p. 101°-102° C.

REFERENCE EXAMPLE 16

(1) 5-Butyl-2,-chloro-2-(2-nitrovinylamino)benzophenone: m.p. 143°-144° C.

(2) 6-Butyl-4-(2-chlorophenyl)-3-nitroquinoline: m.p. 96°-97° C.

(3) 3-Amino-6-butyl-4-(2-chlorophenyl)quinoline: an oil.

REFERENCE EXAMPLE 17

(1) 2'-Chloro-5-fluoro-2-(2-nitrovinylamino)benzophenone: m.p. 118°-119° C.

(2) 4-(2-Chlorophenyl)-6-fluoro-3-nitroquinoline: m.p. 185°-186° C.

(3) 3-Amino-4-(2-chlorophenyl)-6-fluoroquinoline: m.p. 131°-133° C.

REFERENCE EXAMPLE 18

(1) A mixture of 2-amino-2'-chloro-3,5-dimethylbenzophenone (1 g), acetone (50 ml), 20 % hydrochloric acid (20 ml) and methazonic acid (4.5 g, wet) was stirred for 2 hrs. at room temperature and refluxed for 4 hrs. The mixture was diluted with water, and extracted with chloroform. The organic layer was washed with water, dried over anhydrous magnesium sulfate and distilled to remove the solvent. The residue was purified by a column chromatography on silica gel to give 4-(2-chlorophenyl)-6,8-dimethyl-3-nitroquinoline as crystals, which was recrystallized from a mixture of methanol and chloroform. m.p. 130°-131° C. Yield 1.95 g (54.2 %).

(2) In a similar manner as Reference Example 1- 3), 4-(2-chlorophenyl)-6,8-dimethyl-3-nitroquinoline was reduced to give 3-amino-4-(2-chlorophenyl)-6,8-dimethylquinoline. m.p. 152°-154° C. Yield 80.1%.

REFERENCE EXAMPLE 19

The following compounds were obtained in a similar manner as Reference Example 18.

(1) 6-Chloro-4-(2-chlorophenyl)-8-methyl-3-nitroquinoline: m.p. 138°-139° C.

(2) 3-Amino-6-chloro-4-(2-chlorophenyl)-8-methylquinoline: m.p. 138°-139° C.

REFERENCE EXAMPLE 20

The following compounds were obtained in a similar manner as Reference Example 18.

(1) 6,8-Dimethyl-4-(2-methylphenyl)-3-nitroquinoline: m.p. 101°-102° C.

(2) 3-Amino-6,8-dimethyl-4-(2-methylphenyl)quinoline.hydrochloride: m.p. 204°-206° C.

REFERENCE EXAMPLE 21

(1) A mixture of 6-methoxy-2-nitro-4-phenylquinoline (3.50 g) and 47% hydrobromic acid (50 ml) was refluxed for 7 hrs. After cooling, the precipitating crystals were collected by filtration, and recrystallized from acetone to give 6-hydroxy-3-nitro-4-phenylquinoline as yellow needles. Yield 3.01 g (90.7%). m.p. 282°-284° C.

Elemental analysis for $C_{15}H_{10}N_2O_3$: Calculated: C, 67.67; H, 3.79; N, 10.52. Found: C, 67.68; H, 3.79; N, 10.42.

(2) N,N-Dimethylthiocarbamoyl chloride (1.28 g) and 1,4-diazobicyclo [2,2,2] octane (1.05 g) were added to a solution of 6-hydroxy-3-nitro-4-phenylquinoline (2.5 g) in N,N-dimethylformamide (30 ml).

The whole was stirred at room temperature overnight and then poured into ice-water. The resultant precipitate was collected by filtration and recrystallized from acetone to give 6-(N,N-dimethylthiocarbamoyloxy)-3-nitro-4-phenylquinoline as yellow prisms. Yield 1.70 g (51.2%). m.p. 205°-208° C.

Elemental analysis for $C_{18}H_{15}N_3O_3S$: Calculated: C, 61 18; H, 4.28; N, 11.89. Found: C, 61.40; H, 4.28; N, 11.74.

(3) 6-(N,N-Dimethylthiocarbamoyloxy)-3-nitro-4-phenylquinoline (1.50 g) was heated for 3 hrs. at 215°-220° C. After cooling, it was recrystallized from acetone to give 6-(N,N-dimethylcarbamoylthio)-3-nitro-4-phenylquinoline as pale yellow needles. Yield 1.30 g (86.7%). m.p. 171°-173° C.

Elemental analysis for $C_{18}H_{15}N_3O_3S$: Calculated: C, 61.18; H, 4.28; N, 11.89. Found: C, 61.40; H, 4.28; N, 11.74.

(4) To a solution of 6-(N,N-dimethylcarbamoylthio)-3-nitro-4-phenylquinoline (2.50 g) in dioxane (100 ml) were added 2N-NaOH (50 ml) and methanol (20 ml), and the whole was stirred for 7 hrs. at room temperature. After diluted with water, the mixture was acidified with hydrochloric acid. The precipitating crystals were collected by filtration and recrystallized from acetone to give 6-mercapto-3-nitro-4-phenylquinoline as yellow needles. Yield 1.68 g (84.0%). m.p. 160°-163° C.

Elemental analysis for $C_{15}H_{10}N_2O_2S$: Calculated: C, 63,82; H, 3.57; N, 9.92. Found: C, 63.80; H, 3.49; N, 9.68.

(5) To a solution of 6-mercapto-3-nitro-4-phenylquinoline (1.55 g) in dioxane (30 ml) were added a solution of potassium carbonate (1.14 g) in water (10 ml) and methyl iodide (1.17 g), and the whole was stirred for 2.5 hrs. at room temperature. After dilution with water, the mixture was acidified with hydrochloric acid, and the precipitating crystals were collected by filtration and recrystallized from acetone to give 6-methylthio-3-nitro-4-phenylquinoline as yellow needles. Yield 1.39 g (85.3%). m.p. 131°-133° C.

Elemental analysis for $C_{16}H_{12}N_2O_2O$: Calculated: C, 64.85; H, 4.08; N, 9.45. Found: C, 64.77; H, 4.07; N, 9.42.

(6) In a similar manner as Reference Example 1-(3), 6-methylthio-3-nitro-4-phenylquinoline (1.20 g) was reduced to give 3-amino-6-methylthio-4-phenylquinoline as colorless rods. Yield 0.77 g (71.3%). m.p. 135°-137° C.

Elemental analysis for $C_{16}H_{14}N_2S$: Calculated: C, 72.15; H, 5.30; N, 10.52. Found: C, 72.00; H, 5.31; N, 10.52.

REFERENCE EXAMPLE 22

(1) To a solution of 3-acetamido-6-chloro-4-phenylquinoline (1 g) in N,N-dimethylformamide (10 ml) was added 60% sodium hydride in oil (0.15 g). After stirring for 30 mins. at room temperature, to the mixture was added dropwise methyl iodide(0.25 ml) under stirring and then followed by stirring for 1 hr. at room temperature. After the mixture was diluted with water, the resultant precipitate was collected by filtration, and recrystallized from a mixture of methanol and chloroform to give 6-chloro-3-(N-methylacetamido)-4-phenylquinoline as colorless crystals. Yield 0.96 g (91.4%). m.p. 268°-270° C.

Elemental analysis for $C_{18}H_{15}ClN_2O$: Calculated: C, 69.57; H, 4.86; N, 9.01. Found: C, 69.52; H, 4.85; N, 8.89.

(2) A mixture of 6-chloro-3-(N-methylacetamido)-4-phenylquinoline (0.9 g), methanol (5 ml) and conc. hydrochloric acid (5 ml) was refluxed for 5 hrs. It was diluted with water and neutralized with aqueous sodium hydroxide solution. The resultant precipitate was collected by filtration and recrystallized from methanol to give 6-chloro-3-methylamino-4-phenylquinoline as pale yellow crystals. Yield 0.65 g (83.5%). m.p. 139°–140° C.

Elemental analysis for $C_{16}H_{13}ClN_2$: Calculated: C, 71.51; H, 4.88; N, 10.42. Found: C, 71.71; H, 4.87; N, 10.45.

The compounds of the following Reference Examples 23–26 were obtained in a manner similar to that described in Reference Example 22.

REFERENCE EXAMPLE 23

(1) 6-Chloro-3-(N-ethylacetamido)-4-phenylquinoline: m.p. 227°–228° C.

(2) 6-Chloro-3-ethylamino-4-phenylquinoline: m.p. 106°–107° C.

REFERENCE EXAMPLE 24

(1) 3-(N-Butylacetamido)-6-chloro-4-phenylquinoline: m.p. 108°–110° C.

(2) 3-Butylamino-6-chloro-4-phenylquinoline: m.p. 71°–73° C.

REFERENCE EXAMPLE 25

(1) 6-Chloro-3-(N-heptylacetamido)-4-phenylquinoline: an oil.

(2) 6-Chloro-3-heptylamino-4-phenylquinoline: m.p. 62°–63° C.

REFERENCE EXAMPLE 26

(1) 3-(N-Benzylacetamido)-6-chloro-4-phenylquinoline: m.p. 57°–61° C.

(2) 3-Benzylamino-6-chloro-4-phenylquinoline: m.p. 140°–141° C.

REFERENCE EXAMPLE 27

The following compounds were obtained in a similar manner as Reference Example 1.

(1) 5-Chloro-2-(2-nitrovinylamino)-2'-methylthiobenzophenone: m.p. 188°–190° C.

(2) 6-Chloro-4-(2-methylthiophenyl)-3-nitroquinoline: m.p. 180°–182° C.

(3) 3-Amino-6-chloro-4-(2-methylthiophenyl)quinoline: m.p. 153°–155° C.

REFERENCE EXAMPLE 28

6-Mercapto-3-nitro-4-phenylquinoline (1.00 g) was dissolved in a mixture of 2N-sodium hydroxide (20 ml) and dioxane (20 ml), and into the solution was introduced chlorodifluoromethane gas for 2 hrs. at 75°–80° C. The reaction mixture was diluted with water and extracted with chloroform. The extract was washed with aqueous 2N-sodium hydroxide solution and water, dried over anhydrous magnesium sulfate, and distilled to remove the solvent. The residue was recrystallized from isopropyl ether to give 6-difluoromethylthio-3-nitro-4-phenylquinoline as yellow prisms. Yield 948 mg (80.5%). m.p. 101°–103° C.

Elemental analysis for $C_{16}H_{10}F_2N_2O_2S$: Calculated: C, 57.83; H, 3.03; N, 8.43. Found: C, 57 92; H 3.13; N 8.37.

(2) In a similar manner as Reference Example 1-(3), 6-difluoromethylthio-3-nitro-4-phenylquinoline obtained as the above, was reduced to give 3-amino-6-difluoromethylthio-4-phenylquinoline as an oil. This product was used as the starting material without purification.

REFERENCE EXAMPLE 29

(1) 6-Hydroxy-3-nitrophenylquinoline (1.00 g) was dissolved in a mixture of 2N-sodium hydroxide (20 ml) and dioxane (20 ml), and chlorodifluoromethane gas was introduced into the solution for 8 hrs. at 75°–80° C. The mixture was treated in a similar manner as Reference Example 28-(1) to give 6-difluoromethoxy-3-nitro-4-phenylquinoline as pale brown prisms. Yield 794 mg (66.8%). m.p 112°–114° C.

Elemental analysis for $C_{16}H_{10}F_2N_2O$: Calculated: C, 60.76; H, 3.19; N, 8.86. Found: C, 61.04; H, 3.24; N, 8.80.

(2) In a similar manner as Reference Example 1-(3), 6-difluoromethoxy-3-nitro-4-phenylquinoline obtained as the above, was reduced to give 3-amino-6-difluoromethoxy-4-phenylquinoline as an oil. This product was used as the starting material without purification.

REFERENCE EXAMPLE 30

The following compounds were obtained in a manner similar to that described in Reference Example 18.

(1) 8-Chloro-4-(2-chlorophenyl)-6-methyl-3-nitroquinoline m.p. 152°–154° C.

(2) 3-Amino-8-chloro-4-(2-chlorophenyl)-6-methylquinoline: m.p. 148°–149° C.

REFERENCE EXAMPLE 31

The following compounds were obtained in a manner similar to that described in Reference Example 22.

(1) 3-(N-Butylacetamido)-6-chloro-4-(2-chlorophenyl)quinoline: m.p. 108°–109° C.

(2) 3-Butylamino-6-chloro-4-(2-chlorophenyl)quinoline: m.p. 90°–91° C.

REFERENCE EXAMPLE 32

(1) A mixture of diethyl (2-benzoyl-4-chlorophenyl)aminomethylenemalonate (7.0 g), lithium chloride (3.7 g) and dimethyl sulfoxide (70 ml) was heated for 1.5 hrs. at 180° C. The mixture was diluted with water to give ethyl 6-chloro-4-phenyl-3-quinolinecarboxylate as crystals (3.8 g, 70.0%), which was recrystallized from ethanol as needles. m.p. 123°–124° C.

Elemental analysis for $C_{18}H_{14}ClNO_2$: Calculated: C, 69.35; H, 4.53; N, 4.49. Found: C, 69.32; H, 4.48; N, 4.31.

(2) A mixture of ethyl 6-chloro-4-phenyl-3-quinolinecarboxylate (2.5 g), potassium hydroxide (2.24 g) and ethanol (25 ml) was heated for 10 mins. at 80° C. The mixture was diluted with water and acidified with hydrochloric acid to give 6-chloro-4-phenyl-3-quinolinecarboxylic acid as crystals (2.20 g, 96.9%), which was recrystallized from a mixture of methanol and chloroform as pale yellow prisms. m.p. 269°–270° C.

Elemental analysis for $C_{16}H_{10}ClNO_2$: Calculated: C, 67.74; H, 3.55; N, 4.94. Found: C, 67.77; H, 3.52; N, 4.94.

REFERENCE EXAMPLE 33

(1) A mixture of 2-amino-2'-chloro-3,5-dimethylbenzophenone (2.59 g), methyl 3,3-dimethoxypropionate (3.7 g), p-toluenesulfonic acid hydrate (0.19 g) and benzene (30 ml) was refluxed for 16 hrs., with removal of water by a Dien-Stark apparatus. The mixture was distilled to remove the solvent, and the residue was purified by a column chromatography on silica gel to give methyl 4-(2-chlorophenyl)-6,8-dimethyl-3-quinolinecarboxylate as crystals (1.90 g, 58.5%), which was recrystallized from isopropyl ether as colorless prisms. m.p. 117°–118° C.

Elemental analysis for $C_{19}H_{16}ClNO_2$: Calculated: C, 70.50; H, 4.95; N, 4.30. Found: C, 70.14; H, 4.97; N, 4.27.

(2) A mixture of methyl 4-(2-chlorophenyl)-6,8-dimehtyl-3-quinolinecarboxylate (0.98 g), potassium hydroxide (0.5 g) and 80% ethanol (10 ml) was refluxed for 15 mins. The mixture was diluted with water and acidified with hydrochloric acid to give 4-(2-chlorophenyl)-6,8-dimethyl-3-quinolinecarboxylic acid as crystals (0.90 g, 96.8%), which was recrystallized from ethanol as colorless prisms. m.p. 234°–235° C.

Elemental analysis for $C_{18}H_{14}ClNO_2$: Calculated: C, 69.35; H, 4.53; N, 4.49. Found: C, 69.10; H, 4.53; N, 4.41.

REFERENCE EXAMPLE 34

1-Morpholino-2-nitroethene (9.48 g) was added to a mixture of 2-amino-2'-choloro-3,5-dimethylbenzophenone (15.54 g), 6N-hydrochloric acid (60 ml) and ethyl acetate (180 ml), and the whole was stirred at 60°–70° C. To the mixture was added each of 1-morpholino-2-nitroethene (9.48 g) after 2 and 4 hrs. The whole was stirred for an additional 4 hrs., diluted with water and extracted with ethyl acetate. The extract was washed with water, sodium hydrogen carbonate solution and water successively, dried over anhydrous sulfate and distilled to remove the solvent. The residue was recrystallized from ethanol to give 4-(2-chlorophenyl)-6,8-dimethyl-3-nitroquinoline as yellow crystals (15.75 g, 84.1%). m.p. 131°–132° C. This substance was identical with that obtained in Reference Example 18-(1).

REFERENCE EXAMPLE 35

(1) 6-Chloro-4-(3,4-dimethoxyphenyl)-3-nitroquinoline was obtained in a manner similar to that described in Reference Example 34. m.p. 188°–190° C. Yield 83.5%.

(2) In a similar manner as Reference Example 1-(2), 6-chloro-4-(3,4-dimethoxyphenyl)-3-nitroquinoline was reduced to give 3-amino-6-chloro-4-(3,4-dimethoxyphenyl)quinoline. m.p. 187°–190° C. Yield 92.9%.

The compounds of the following Reference Examples 36–37 were obtained in a manner similar to that described in Reference Example 35.

REFERENCE EXAMPLE 36

(1) 4-(2-Chlorophenyl)-6,7-dimethyl-3-nitroquinoline: m.p 156°–157° C. Yield 50.9%.
(2) 3-Amino-4-(2-chlorophenyl)-6,7-dimethylquinoline: m.p. 194°–195° C. Yield 68.9%.

REFERENCE EXAMPLE 37

(1) 4-(2-Chlorophenyl)-6,7,8-trimethyl-3-nitroquinoline: m.p. 190°–191° C. Yield 53.3%.
(2) 3-Amino-4-(2-chlorophenyl)-6,7,8-trimethylquinoline: m.p. 116°–118° C. Yield 79.8%.

REFERENCE EXAMPLE 38

A mixture of 2,6-di-tert-butyl-4-methylphenol (2.34 g), N-bromosuccinimide (1.88 g) and carbon tetrachloride (25 ml) was refluxed for 2 hrs. The mixture was filtered to remove the insoluble precipitate to give a solution of 4-bromomethyl-2,6-di-tert-butylphenol. To the solution was added 3-amino-4-(2-chlorophenyl)-6,8-dimethylquinoline (2.0 g), and the whole was stirred for 5 hrs. at room temperature. The mixture was diluted with chloroform, washed with water, dried over anhydrous magnesium sulfate and distilled to remove the solvent. The residue was purified by a column chromatography on silica gel and recrystallized from a mixture of acetone and isopropyl ether to give 4-(2-chlorophenyl)-3-(2,6-di-tert-butyl-4-hydroxyphenyl)amino-6,8-dimethylquinoline as colorless prisms (1.59 g, 44.9%). m.p. 183°–185° C.

Elemental analysis for $C_{32}H_{37}ClNO_2$: Calculated: C, 76.70; H, 7.44; N, 5.59. Found: C, 76.70; H, 7.53; N, 5.52.

REFERENCE EXAMPLE 39

(1) A mixture of 2-amino-2'-chloro-3,5-dimethylbenzophenone (20.0 g), 2,2-dimethoxypropionitrile (11.5 g), p-toluenesulfonic acid hydrate (1.46 g) and toluene (200 ml) was refluxed for 3 hrs., with removal of water by a Dean-Stark apparatus. The mixture was washed with sodium hydrogen carbonate solution and water, dried over anhydrous magnesium sulfate and distilled to remove the solvent. The resultant precipitate was collected by filtration and washed with hexane to give 4-(2-chlorophenyl)-6,8-dimethyl-3-quinolinecarbonitrile (20.7 g, 92.0%), which was recrystallized from ethanol to give pale yellow plates. m.p. 153°–154° C.

Elemental analysis for $C_{18}H_{13}ClN_2$: Calculated: C, 73.85; H, 4.48; N, 9.57. Found: C, 73.66; H, 4.42; N, 9.54.

(2) A mixture of 4-(2-chlorophenyl)-6,8-dimethyl-3-quinolinecarbonitrile (0.5 g), 6N-sodium hydroxide (1.5 ml) and 2-methoxyethanol (3 ml) was refluxed under stirring for 8 hrs. The mixture was diluted with water and acidified with hydrochloric acid. The resultant precipitate was collected by filtration to give 4-(2-chlorophenyl)-6,8-dimethyl-2-quinolinecarboxylic acid (0.46 g, 86.8%), which was recrystallized from ethanol to give colorless prisms. m.p. 234°–235° C. This substance was identical with that obtained in Reference Example 33.

REFERENCE EXAMPLE 40

(1) A mixture of 4-(2-chlorophenyl)-6,8-dimethyl-3-quinolinecarbonitrile (17.6 g), obtained in Reference Example 39 - (1), and 97% sulfuric acid (120 ml) was stirred for 24 hrs. at room temperature. The mixture was poured into ice-water, made basic with aqueous ammonia and then extracted with ethyl acetate. The extract was washed with water, dried over anhydrous magnesium sulfate and distilled to remove the solvent. To the residue was added methanol to give 4-(2-chlorophenyl)-6,8-dimethyl-3-quinolinecarboxamide.methanol solvate as crystals (18.5 g, 90.2%), which was recrystallized from methanol to give colorless prisms (18.5 g, 90.2%). m.p. 163°–164° C.

Elemental analysis for $C_{18}H_{15}ClN_2O \cdot CH_4O$: Calculated: C, 66.57; H, 5.59; N, 8.17. Found: C, 66.75; H, 5.52; N, 8.19.

(2) Bromine (3.2 ml) was added dropwise to a solution of sodium hydroxide (10.4 g) in water (100 ml) under ice cooling and stirring. Then, to the mixture was added dropwise a solution of 4-(2-chlorophenyl)-6,8-dimethyl-3-quinolinecarboxamide methanol solvate (18.5 g) in dioxane (100 ml), and the whole was stirred for 30 mins. at room temperature and for 40 mins. at 90° C. The mixture was adjusted to pH 1 with 6N-hydrochloric acid, stirred for 30 mins. at room temperature and then filtered to remove a small amount of the resultant red precipitate. The filtrate was made basic with 6N-sodium hydxide solution, diluted with water and extracted with ethyl acetate. The extract was washed with water, dried over anhydrous magnesium sulfate and then distilled to remove the solvent. The residue was recrystallized from hexane to give 3-amino-4-(2-chlorophenyl)-6,8-dimethylquinoline (14.0 g, 91.7%). m.p. 151°-152° C. This product was identical with that obtained in Reference Example 18.

REFERENCE EXAMPLE 41

(1) A mixture of 5-chloro-2-tosylaminobenzoic acid (14.0 g), thionylchloride (30 ml) and N,N-dimethylformamide (0.5 ml) was refluxed for 40 mins. and concentrated to dryness under reduced pressure. The residue was dissolved in 1,2-dichloroethane (100 ml), and to the solution was added anhydrous aluminium chloride (6.88 g). After stirring for 10 mins. at room temperature, to the mixture was added 1,2,3-trimethoxybenzene (8.67 g), and the whole was stirred for 10 mins. at room temperature and then refluxed for 45 mins. After cooling, 2N-hydrochloric acid was added to the mixture, and the whole was stirred for 30 mins. at room temperature. The organic layer was separated and extracted with dil. sodium hydroxide solution. The alkaline layer was acidified with hydrochloric acid and extracted with chloroform. The chloroform layer was washed with water, dried over anhydrous magnesium sulfate and distilled to removed the solvent. The residue was recrystallized from acetone to give 2-tosylamino-5-chloro-2'-hydroxy-3',4'-dimethoxybenzophenone as prisms (5.89 g, 29.6%). m.p. 185°-187° C.

Elemental analysis for $C_{22}H_{20}ClNO_6S$: Calculated: C, 57.21; H, 4.36; N, 3.03. Found: C, 57.16; H, 4.24; N, 3.17.

(2) A mixture of 2-tosylamino-5-chloro-2'-hydroxy-3', 4'-dimethoxybenzophenone (5.89 g) and 70% sulfuric acid (50 ml) was heated for 1 hr. at 90° C. The whole was diluted with water and extracted with chloroform. The chloroform layer was washed with water, dried over anhydrous magnesium sulfate and concentrated. The residue was purified by a column chromatography on silica gel and recrystallized from a mixture of ether and hexane to give 2-amino-5-chloro-2'-hydroxy-3',4'-dimethoxybenzophenone as colorless prisms (3.01 g, 76.8%). m.p. 112°-115° C.

Elemental analysis for $C_{15}H_{14}ClNO_4$: Calculated: C, 58.55; H, 4.59; N, 4.55. Found: C, 58.65; H, 4.61; N, 4.51.

REFERENCE EXAMPLE 42

2-Amino-5-chloro-2'-hydroxy-3',4'-dimethoxybenzophenone, obtained in Reference Example 41, was reacted in a similar manner as Reference Example 41 to give the following compounds.

(1) 6-Chloro-4-(2-hydroxy-3,4-dimethoxyphenyl)-3-nitroquinoline m.p. 156°-158° C. Yield 91.8%.

(2) 3-Amino-6-chloro-4-(2-hydroxy-3,4-dimethoxyphenyl)quinoline: m.p. 198°-201° C. Yield 60.5%.

REFERENCE EXAMPLE 43

(1) A mixture of 6-chloro-4-(2-hydroxy-3,4-dimethoxyphenyl)-3-nitroquinoline (1.20 g), N,N-dimethylformamide (20 ml), potassium carbonate powder (0.92 g) and methyl iodide (0.41 ml) was stirred for 10 mins. at 0° C. and for 2 hrs. at room temperature, and then diluted with water, extracted with ethyl acetate. The extract was washed with water, dried over anhydrous magnesium sulfate and distilled to remove the solvent. The residue was recrystallized from methanol to give 6-chloro-4-(2,3,4-trimethoxyphenyl)-3-nitroquinoline as yellow crystals (1.12 g, 89.6%). m.p. 114°-116° C.

(2) 6-Chloro-4-(2,3,4-trimethoxyphenyl)-3-nitroquinoline, obtained as above, was reduced in a similar manner as Reference Example 1 - (2) to give 3-amino-6-chloro-4-(2,3,4-trimethoxyphenyl)quinoline. m.p. 180°-181° C. Yield 95.9%.

REFERENCE EXAMPLE 44

The following compounds were obtained in a manner similar to that described in Reference Example 35.

(1) 4-(2-Chlorophenyl)-5-methyl-3-nitroquinoline: m.p. 147°-148° C. Yield 69.8%.

(2) 3-Amino-4-(2-chlorophenyl)-5-methylquinoline: m.p. 152°-153° C. Yield 97.8%.

What we claim is:

1. A quinoline derivative of the formula (I):

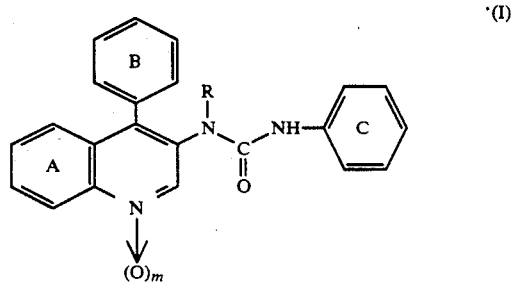

wherein R is a hydrogen atom, or an alkyl group or a phenyl alkyl group having 7 to 9 carbon atoms in which the benzene ring is substituted or unsubstituted; m is 0 or 1; and when m=1, each of rings A, B and C is substituted or unsubstituted; and when m=0, (a) each of rings A and C is substituted or unsubstituted and ring B is substituted, or (b) ring C is substituted with at least one fluorine atom, ring B has no substituent and ring A is substituted or unsubstituted, the substituents for the A, B and C rings numbering from 1 to 4 and being selected from the group consisting of a halogen atom, an optionally halogenated lower alkyl group, an optionally halogenated lower alkoxy group, an optionally halogenated lower alkylthio group, nitro group, a carboxyl group, an esterified carboxyl group, hydroxy group, a C1-4 acyloxy group selected from the group consisting of formyloxy, acetyloxy, propionyloxy, and butyryloxy, and an aliphatic acyl group having 1-3 carbon atoms selected from the group consisting of formyl, acetyl, and propionyl;

subject to at least one of the following provisos:
(a) the ring A has a substituent at the 6-, 8-, or both positions of the quinoline nucleus,
(b) the ring B has a substituent at the 2-position, or
(c) the ring C has a substituent at the 2-, 4-, or both positions;

or its salt.

2. A quinoline derivative of claim 1 wherein R is hydrogen, an alkyl group having 1-8 carbon atoms, or a phenylalkyl group having 7-9 carbon atoms.

3. A quinoline derivative of claim 1, in which each of the rings A, B and C has one to four substituents selected from the group consisting of a halogen atom, an optionally halogenated lower alkyl group, an optionally halogenated lower alkoxy group, an optionally halogenated lower alkylthio group, nitro group, a carboxyl group, an esterified carboxyl group, hydroxy group, a $C_{1-4}$ acyloxy group and an aliphatic acyl group having 1-3 carbon atoms.

4. A quinoline derivative of the formula (I$^a$):

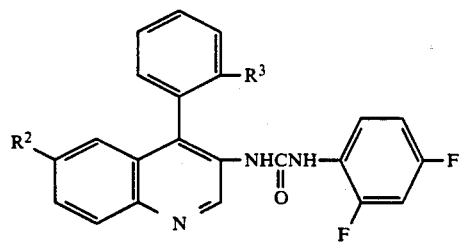

wherein R$^2$ and R$^3$ are, the same or different, a halogen atom or an alkyl group having 1–4 carbon atoms.

5. A quinoline derivative of the formula (I$^b$):

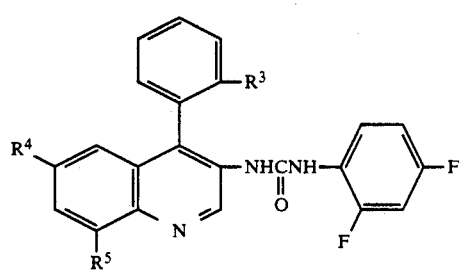

wherein R$^4$ and R$^5$ are, the same or different, an alkyl group having 1–4 carbon atoms, and R$^3$ is a halogen atom or an alkyl group having 1–4 carbon atoms.

6. A quinoline derivative which is
6-chloro-4-(2-chlorophenyl)-3-[3-(2,4-difluorophenyl) ureido]quinoline,
6-chloro-3-[3-(2,4-difluorophenyl)ureido]-4-(2-methylphenyl)quinoline,
3-[3-(2,4-difluorophenyl)ureido]-6-methyl-4-(2-methylphenyl)quinoline,
4-(2-chlorophenyl)-3-[3-(2,4-difluorophenyl)ureido]-6,8-dimethylquinoline,
4-(2-chlorophenyl)-3-[3-(2,4-difluorophenyl)ureido]-6-ethylquinoline,
4-(2-chlorophenyl)-3-[3-(2,4-difluorophenyl)ureido]-6-fluoroquinoline,
3-[3-(2,4-difluorophenyl)ureido]-6-methyl-4-(2-methylphenyl)quinoline,
4-(2-chlorophenyl)-3-[3-(2,6-dimethylphenyl)ureido]-6,8-dimethylquinoline or 4-(2-chlorophenyl)-3-[3-(4-hydroxy-3,5-dimethylphenyl)ureido]-6,8-dimethylquinoline.

7. A composition for the inhibition of acyl-CoA: cholesterol-acyl-transferase which comprises a quinoline derivative of the formula (I) as claimed in claim 1 and a pharmaceutically acceptable diluent or carrier.

8. A method of inhibiting acyl-CoA: cholesterol-acyl-transferase which comprises administering to a patient in need thereof an effective amount of a quinoline derivative of the formula (I):

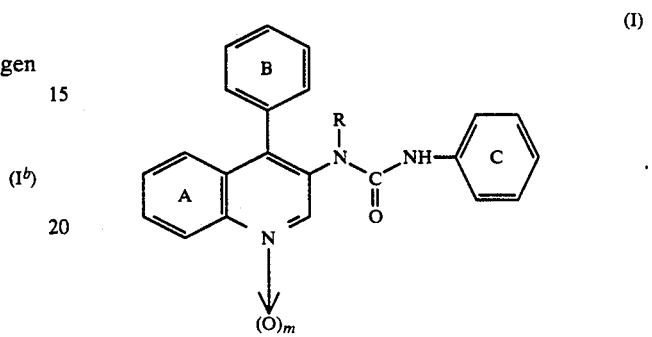

wherein R is a hydrogen atom, or an alkyl group or a phenyl alkyl group having 7 to 9 carbon atoms in which the benzene ring is substituted or unsubstituted, m is 0 or 1; and when m=1, each of rings A, B and C is substituted or unsubstituted; and when m=0, (a) each of rings A and C is substituted or unsubstituted and ring B is substituted, or (b) ring C is substituted with at least one fluorine atom, ring B has no substituent and ring A is substituted or unsubstituted, the substituents for the A, B and C rings numbering from 1 to 4 and being selected from the group consisting of a halogen atom, an optionally halogenated lower alkyl group, an optionally halogenated lower alkoxy group, an optionally halogenated lower alkylthio group, nitro group, a carboxyl group, an esterified carboxyl group, hydroxy group, A C1–4 acyloxy group selected from the group consisting of formyloxy, acetyloxy, propionyloxy, and butyryloxy and an aliphatic acyl group having 1–3 carbon atoms selected from the group consisting of formyl, acetyl, and propionyl or a pharmaceutically acceptable salt thereof.

9. 4-(2-chlorophenyl)-3-[3-(2,4-difluorophenyl)ureido-6,7-dimethylquinoline.

* * * * *

UNITED STATES PATENT AND TRADEMARK OFFICE
CERTIFICATE OF CORRECTION

PATENT NO. : 5,254,565
DATED : October 19, 1993
INVENTOR(S) : Kanji MEGURO et al.

It is certified that error appears in the above-indentified patent and that said Letters Patent is hereby corrected as shown below:

In claim 1, line 44, col. 42, change "C1-4" to --$C_{1-4}$--;

In claim 8, line 40, col. 44, change "A C1-4" to --a $C_{1-4}$--.

Signed and Sealed this

Thirteenth Day of September, 1994

Attest:

BRUCE LEHMAN

*Attesting Officer*   *Commissioner of Patents and Trademarks*